US012618040B2

(12) United States Patent
Hincapie et al.

(10) Patent No.: US 12,618,040 B2
(45) Date of Patent: May 5, 2026

(54) PRODUCT QUALITY ATTRIBUTE MEASUREMENT

(71) Applicant: Genzyme Corporation, Cambridge, MA (US)

(72) Inventors: Marina Hincapie, Framingham, MA (US); Victoria Berger, North Chelmsford, MA (US)

(73) Assignee: GENZYME CORPORATION, Cambridge, MA (US)

( * ) Notice: Subject to any disclaimer, the term of this patent is extended or adjusted under 35 U.S.C. 154(b) by 1089 days.

(21) Appl. No.: 17/028,535

(22) Filed: Sep. 22, 2020

(65) Prior Publication Data

US 2021/0087514 A1     Mar. 25, 2021

Related U.S. Application Data

(60) Provisional application No. 62/904,682, filed on Sep. 23, 2019.

(51) Int. Cl.
*G01N 30/46* (2006.01)
*C07K 16/22* (2006.01)
(Continued)

(52) U.S. Cl.
CPC ............. *C12M 41/30* (2013.01); *C07K 16/22* (2013.01); *C12M 33/00* (2013.01); *C12M 41/00* (2013.01);
(Continued)

(58) Field of Classification Search
CPC ....... C12M 41/00; C12M 41/30; C07K 16/22; G01N 30/08; G01N 30/20; G01N 30/46;
(Continued)

(56) References Cited

U.S. PATENT DOCUMENTS

| | | | |
|---|---|---|---|
| 11,101,121 B2 | 8/2021 | Hasegawa |
| 2002/0084222 A1 | 7/2002 | Brann |

(Continued)

FOREIGN PATENT DOCUMENTS

| | | |
|---|---|---|
| CN | 102574026 | 7/2012 |
| CN | 105377874 | 3/2016 |

(Continued)

OTHER PUBLICATIONS

Microsaic Systems, "3 reasons why you should upgrade from UV detection to Mass Spectrometry", Microsaic Systems. Sep. 10. (Year: 2019).*

(Continued)

*Primary Examiner* — Benjamin L Lebron
(74) *Attorney, Agent, or Firm* — MH2 Technology Law Group, LLP

(57) ABSTRACT

Systems for measuring a product quality attribute of an analyte of a biological sample include a first flow control device, a sample purification device, a second flow control device in fluid communication with first and second sample analyzers, where the first sample analyzer includes a first chromatography column, and a control unit configured so that during operation of the system, the control unit adjusts a configuration of the second flow control device to direct a portion of the biological sample to one of the first and second sample analyzers, and determines a product quality attribute of an analyte of the biological sample based on an analysis of the portion of the biological sample by the one of the first and second sample analyzers.

22 Claims, 13 Drawing Sheets

FIG. 1

(51) Int. Cl.

| | | |
|---|---|---|
| *C12M 1/26* | (2006.01) | |
| *C12M 1/34* | (2006.01) | |
| *G01N 30/08* | (2006.01) | |
| *G01N 30/20* | (2006.01) | |
| *G01N 30/88* | (2006.01) | |
| *G01N 33/68* | (2006.01) | |

(52) U.S. Cl.
CPC ............. *G01N 30/08* (2013.01); *G01N 30/20* (2013.01); *G01N 30/46* (2013.01); *G01N 30/88* (2013.01); *G01N 33/6854* (2013.01); *G01N 2030/085* (2013.01); *G01N 2030/201* (2013.01); *G01N 2030/8886* (2013.01); *G01N 2333/495* (2013.01)

(58) Field of Classification Search
CPC ............... G01N 30/88; G01N 33/6854; G01N 2030/085; G01N 2030/201; G01N 2030/8886; G01N 2333/495
See application file for complete search history.

(56) References Cited

U.S. PATENT DOCUMENTS

| | | | |
|---|---|---|---|
| 2002/0155541 A1 | 10/2002 | Naughton et al. | |
| 2008/0249289 A1 | 10/2008 | Axen et al. | |
| 2012/0164066 A1 | 6/2012 | Greene et al. | |
| 2014/0255994 A1 | 9/2014 | Konstantinov et al. | |
| 2015/0203505 A1 | 7/2015 | Kanayama et al. | |
| 2017/0137500 A1 | 5/2017 | Allison et al. | |
| 2017/0153210 A1* | 6/2017 | Eriksson ............... | B01D 15/34 |
| 2018/0339244 A1 | 11/2018 | Hubbuch et al. | |
| 2019/0272894 A1 | 9/2019 | Wasalathanthri et al. | |
| 2020/0360894 A1 | 11/2020 | Norinobu | |
| 2021/0171572 A1 | 6/2021 | Vetter et al. | |

FOREIGN PATENT DOCUMENTS

| | | |
|---|---|---|
| CN | 106661083 | 5/2017 |
| CN | 109313419 | 2/2019 |
| JP | 2013-523690 A | 9/2013 |
| JP | 2015-052533 A | 3/2015 |
| JP | 2016-510981 A | 4/2016 |
| JP | 2016-217836 A | 12/2016 |
| JP | 2017-515501 A | 6/2017 |
| JP | 2019-506406 A | 3/2019 |
| TW | 201811816 A | 4/2018 |
| TW | 201920230 A | 6/2019 |
| TW | 201925317 A | 7/2019 |
| WO | 2011121031 A1 | 10/2011 |
| WO | 2014137903 A1 | 9/2014 |
| WO | WO 2014/137903 | 9/2014 |
| WO | WO 2015/166083 | 11/2015 |
| WO | 2017129585 A1 | 1/2017 |
| WO | WO-2017136753 A1 * | 8/2017 ............ G01N 30/72 |
| WO | WO 2018/122196 | 7/2018 |
| WO | WO 2018/153743 | 8/2018 |
| WO | 2018183971 A1 | 10/2018 |
| WO | WO 2018/183971 | 10/2018 |

OTHER PUBLICATIONS

International Preliminary Report on Patentability in International Application No. PCT/US2020/052019, dated Apr. 7, 2022, 10 pages.

Gebauer et al., "Engineered protein scaffolds as next-generation antibody therapeutics", Current Opin. Chem. Biol., 2009, 13:245-255.

Anonymous, "AKTA avant", May 2015, retrieved on Dec. 22, 2020, retrieved from URL <"https://www.cytivalifesciences.com/en/us/shop/chromatography/chromatography-systems/akta-avant-p-06264">, 12 pages.

Chmielowski et al., "Definition and dynamic control of a continuous chromatography process independent of cell culture titer and impurities", Journal of Chromatography, Oct. 2017, 1526:58-69.

PCT International Search Report and Written Opinion in International Application No. PCT/US2020/052019, dated Jan. 18, 2021, 17 pages.

Office Action in Canadian Appln. No. 3,151,967, dated Nov. 1, 2023, 3 pages.

Office Action in Chinese Appln. No. 202080080043.9, dated Nov. 16, 2023, 43 pages (with English translation).

Office Action in Indonesian Appln. No. P00202204701, dated Nov. 24, 2023, 6 pages (with English translation).

Office Action in Taiwan Appln. No. 109132731, dated Dec. 26, 2023, 19 pages (with English translation).

Office Action in Chinese Appln. No. 202080080043.9, dated May 20, 2023, 44 pages (with English translation).

Office Action in Chinese Appln. No. 202080080043.9, dated Jun. 1, 2024, 40 pages (with English translation).

Search Report in Russian Application No. 2022110701 dated Mar. 3, 2024 (with English translation).

Office Action in Japanese Application No. 2022-518266 dated Apr. 5, 2024, 8 pages (with English translation).

Author Unknown (TW Examiner), Taiwan Search Report for Taiwan Appln. No. 113142055, dated Sep. 1, 2025, 2 pages including English translation.

Wong, Javier (Dr.) (SG Authorized Officer), Singapore Written Opinion for Singapore Application No. 11202202744T dated Oct. 2, 2025, 7 pages.

* cited by examiner

| Injection | Dilution | Calculated Mass (µg) | Calculated Concentration (mg/mL) |
|-----------|----------|----------------------|----------------------------------|
| 1 | N/A | 71.2 | 1.42 |
| 2 | N/A | 71.3 | 1.43 |
| 3 | N/A | 71.6 | 1.43 |
| 4 | N/A | 71.5 | 1.43 |
| 5 | N/A | 71.6 | 1.43 |
| 6 | N/A | 69.6 | 1.39 |
| 1 | 1:2 | 37.1 | 1.48 |
| 2 | 1:2 | 37.0 | 1.48 |
| 3 | 1:2 | 37.1 | 1.48 |
| 4 | 1:2 | 37.1 | 1.48 |
| 5 | 1:2 | 37.2 | 1.49 |
| 6 | 1:2 | 37.7 | 1.51 |

Neat SEC Results

| Injection | Dilution | Peak % | | |
| --- | --- | --- | --- | --- |
| | | HMW | Main | LMW |
| 1 | N/A | 1.0 | 98.6 | 0.3 |
| 2 | N/A | 1.2 | 98.6 | 0.2 |
| 3 | N/A | 1.1 | 98.6 | 0.3 |
| 4 | N/A | 1.5 | 97.8 | 0.4 |
| 5 | N/A | 1.5 | 97.8 | 0.4 |
| 6 | N/A | 1.5 | 97.9 | 0.3 |
| | Average | 1.3 | 98.2 | 0.3 |

1:2 Diluted SEC Results

| Injection | Dilution | Peak % | | |
| --- | --- | --- | --- | --- |
| | | HMW | Main | LMW |
| 1 | 1:2 | 0.7 | 98.9 | 0.3 |
| 2 | 1:2 | 0.7 | 98.7 | 0.6 |
| 3 | 1:2 | 0.6 | 98.9 | 0.5 |
| 4 | 1:2 | 0.5 | 99.0 | 0.5 |
| 5 | 1:2 | 0.6 | 98.9 | 0.5 |
| 6 | 1:2 | 0.5 | 99.0 | 0.5 |
| | Average | 0.6 | 98.9 | 0.5 |

PRODUCT QUALITY ATTRIBUTE MEASUREMENT

CROSS-REFERENCE TO RELATED APPLICATIONS

This application claims priority to U.S. Provisional Patent Application Ser. No. 62/904,682, filed Sep. 23, 2019, the entire contents of this application is herein incorporated by reference.

TECHNICAL FIELD

This disclosure relates to systems and methods for product quality attribute measurement for samples including harvested samples from continuous bio-manufacturing systems.

BACKGROUND

Mammalian cells containing a nucleic acid that encodes a recombinant protein are often used to produce therapeutically or commercially important proteins. Integrated, continuous bio-manufacturing is an important aspect of reducing costs associated with therapies based on such proteins. Monitoring systems are used in bio-manufacturing to assess various biological products and process conditions.

SUMMARY

Integrated, continuous bio-manufacturing of therapeutic protein substances and other biological molecules holds tremendous promise for future production of life-saving drugs and enhancing widespread adoption of therapies that rely on the availability of such biological molecules. Two-column and multi-column chromatography systems in a variety of configurations can be used for bio-manufacturing on an industrial scale. In such systems, analysis of eluents from the chromatography systems can be used to determine a variety of product quality attributes to monitor and adjust a wide variety of bioprocess conditions.

This disclosure features methods and systems for determining one or more product quality attributes for analytes in biological samples, including samples harvested from bioreactors and offline samples introduced in series or in parallel into the systems. A variety of product quality attributes can be measured, including but not limited to analyte concentration, analyte charge variants or heterogeneity, analyte aggregation, and analyte integrity or purity. The systems can include sample analyzers with different types of chromatography columns dedicated to the measurement of specific product quality attributes. The measured product quality attributes can be used to provide feedback and control over bio-manufacturing process-related parameters and operations.

In one aspect, the disclosure features systems for measuring a product quality attribute of an analyte of a biological sample, the systems featuring a first flow control device, a sample purification device in fluid communication with the first flow control device, a second flow control device in fluid communication with the first flow control device, with the sample purification device, and with first and second sample analyzers, where the first sample analyzer includes a first chromatography column, and a control unit coupled to the first and second flow control devices and configured so that during operation of the system, the control unit: (a) adjusts a configuration of the first flow control device to direct a portion of a biological sample from the first flow control device into either the sample purification device or into the second flow control device, so that the portion of the biological sample is received in the second flow control device; (b) adjusts a configuration of the second flow control device to direct the portion of the biological sample to one of the first and second sample analyzers; and (c) determines a product quality attribute of an analyte of the biological sample based on an analysis of the portion of the biological sample by the one of the first and second sample analyzers.

Embodiments of the systems can include any one or more of the following features.

The first chromatography column can be a cation exchange chromatography column, a size exclusion chromatography column, or a reversed phase chromatography column. The sample purification device can include an affinity chromatography column.

The second sample analyzer can include a quantification detector configured to generate an electrical signal representative of an amount of an analyte in the biological sample. The first chromatography column can be in fluid communication with the quantification detector, and the quantification detector can be configured to generate an electrical signal representative of an amount of the analyte in an eluate stream from the first chromatography column.

The first sample analyzer can include a quantification detector in fluid communication with the first chromatography column and configured to generate an electrical signal representative of an amount of an analyte in an eluate stream from the first chromatography column. The second sample analyzer can include a second chromatography column, and the second chromatography column can be different from the first chromatography column and can be one of a cation exchange chromatography column, a size exclusion chromatography column, a reversed phase chromatography column, and a hydrophilic interaction chromatography column.

The second flow control device can be in fluid communication with a third sample analyzer that includes a third chromatography column, and the third chromatography column can be different from the first and second chromatography columns and can be one of a cation exchange chromatography column, a size exclusion chromatography column, a reversed phase chromatography column, and a hydrophilic interaction chromatography column.

The second flow control device can be in fluid communication with four additional sample analyzers, each of the four additional sample analyzers featuring a chromatography column that is different from the first chromatography column and from chromatography columns of the others of the four additional sample analyzers.

The product quality attribute of the analyte can be a concentration of the analyte in the biological sample, a measure of aggregation of the analyte in the biological sample, a measure of charge variants or heterogeneity of the analyte in the biological sample, or a measure of purity or integrity of the analyte in the biological sample.

The affinity chromatography column can be one of a Protein A chromatography column, a Protein G chromatography column, and a receptor binding column. The analyte can include a protein (e.g., an antibody) in the biological sample.

The systems can include a column manager in fluid communication with the first and second sample analyzers and with the second flow control device, and coupled to the control unit, where the control unit is configured to adjust a configuration of the column manager to direct the portion of the biological sample into one of the first and second sample analyzers.

The systems can include a column manager in fluid communication with the first, second, and third sample analyzers and with the second flow control device, and coupled to the control unit, where the control unit can be configured to adjust a configuration of the column manager to direct the portion of the biological sample into one of the first, second, third, and fourth sample analyzers.

The portion of the biological sample can be a first portion and the product quality attribute can be a first product quality attribute, and the control unit can be configured so that during operation of the system, the control unit: (d) adjusts a configuration of the first flow control device to direct a second portion of the biological sample from the first flow control device into either the sample purification device or into the second flow control device, so that the second portion of the biological sample is received in the second flow control device; (e) adjusts a configuration of the second flow control device to direct the second portion of the biological sample to one of the first and second sample analyzers that did not receive the first portion of the biological sample; and (f) determines a second product quality attribute of the analyte of the biological sample based on an analysis of the second portion of the biological sample by the one of the first and second sample analyzers that received the second portion of the biological sample. The first and second product quality attributes can be different, and the first and second product quality attributes can each be selected from the group consisting of a concentration of the analyte in the biological sample, a measure of aggregation of the analyte in the biological sample, a measure of charge variants or heterogeneity of the analyte in the biological sample, and a measure of purity or integrity of the analyte in the biological sample.

The portion of the biological sample can be a first portion and the product quality attribute can be a first product quality attribute, and the control device can be configured to repeat steps (a)-(c) with another portion of the biological sample to determine two different product quality attributes for the analyte of the biological sample.

The portion of the biological sample can be a first portion and the product quality attribute can be a first product quality attribute, and the control device can be configured to repeat steps (a)-(c) with two other portions of the biological sample to determine three different product quality attributes for the analyte of the biological sample.

The portion of the biological sample can be a first portion and the product quality attribute can be a first product quality attribute, and the control device can be configured to repeat steps (a)-(c) with three other portions of the biological sample to determine four different product quality attributes for the analyte of the biological sample.

The product quality attributes can each be selected from the group consisting of a concentration of the analyte in the biological sample, a measure of aggregation of the analyte in the biological sample, a measure of charge variants or heterogeneity of the analyte in the biological sample, and a measure of purity or integrity of the analyte in the biological sample.

The systems can include a sampling device coupled to the control unit and configured to receive the biological sample, and to deliver the portion of the biological sample to the first fluid control device. The sampling device can include a container interface configured to receive the biological sample in a container. The sampling device can include a fluidic channel configured to receive the biological sample, and the control unit can be configured so that during operation of the system, the control unit transmits a signal to the sampling device to cause the sampling device to discharge the portion of the biological sample from the fluidic channel into the first flow control device.

The systems can include a pump in fluid communication with the second flow control device, with the first and second sample analyzers, and with first and second buffer reservoirs associated respectively with the first and second sample analyzers, where the control unit and pump are configured so that during operation of the system, the pump delivers a buffer solution to the one of the first and second sample analyzers from a corresponding associated buffer reservoir when the portion of the biological sample is directed into the one of the first and second sample analyzers.

The systems can include a pump in fluid communication with the second flow control device, with the first, second, and third sample analyzers, and with first, second, and third buffer reservoirs associated respectively with the first, second, and third sample analyzers, where the control unit and pump are configured so that during operation of the system, the pump delivers a buffer solution to the one of the first, second, and third sample analyzers from a corresponding associated buffer reservoir when the portion of the biological sample is directed into the one of the first, second, and third sample analyzers.

The systems can include a pump in fluid communication with the second flow control device, the first sample analyzer, and with a buffer reservoir associated with the first sample analyzer, where the first chromatography column is a cation exchange column, and where the control unit and pump are configured so that during operation of the system, the pump delivers an acetate buffer to the first chromatography column to propagate the portion of the biological sample along the first chromatography column. The acetate buffer can have a pH of 4.0 or less.

The biological sample can be a harvest medium extracted from a bioreactor. The biological sample can be an intermediate or product solution from a bio-manufacturing system. The biological sample can be a portion of a cell culture.

The quantification detector can include a diode array detector, a spectrometric detector configured to measure absorbance information for the portion of the biological sample, a fluorescence detector, and/or a mass spectrometric detector.

Embodiments of the systems can also include any of the other features described herein, including any combinations of features individually disclosed in different embodiments, except as expressly stated otherwise.

In another aspect, the disclosure features systems for measuring product quality attributes for an analyte of a biological sample, the systems featuring a first flow control device, a sample purification device that includes a purification chromatography column in fluid communication with the first flow control device, a second flow control device in fluid communication with the first flow control device and with the sample purification device, a first sample analyzer that includes a first chromatography column in fluid communication with the second flow control device, a second sample analyzer that includes a second chromatography column in fluid communication with the second flow control device, a third sample analyzer that includes a third chromatography column in fluid communication with the second flow control device, a fourth sample analyzer that includes a quantification detector, and a control unit coupled to the first and second flow control devices and configured so that during operation of the system, the control unit: (a) adjusts a configuration of the first flow control device to direct a first portion of a biological sample from the first flow control device into either the sample purification device or into the second flow control device, so that the portion of the biological sample is received in the second flow control device; (b) adjusts a configuration of the second flow control device to direct the first portion of the biological sample to one of the first, second, third, and fourth sample analyzers; (c) determines a first product quality attribute of an analyte of the biological sample based on an analysis of the portion of the biological sample by the one of the first, second, third, and fourth sample analyzers; and (d) repeats steps (a)-(c) with three additional portions of the biological sample, adjusting the configuration of the second flow control device so that each portion of the biological sample is directed to a different one of the sample analyzers, to determine a total of four product quality attributes of the analyte of the biological sample.

Embodiments of the systems can include any one or more of the following features.

Each of the four product quality attributes can be different. Each of the first, second, and third chromatography columns can be a different type of column. The first chromatography column can be a cation exchange column, the second chromatography column can be a size exclusion column, and the third chromatography column can be a reversed phase column or a hydrophilic interaction column.

The first sample analyzer can determine information about a measure of charge variants or heterogeneity of the analyte in the biological sample, the second sample analyzer can determine information about a measure of aggregation of the analyte in the biological sample, the third sample analyzer can determine information about a measure of purity or integrity of the analyte in the biological sample, and the fourth sample analyzer can determine information about a concentration of the analyte in the biological sample.

The four product quality attributes can include a measure of charge variants or heterogeneity of the analyte in the biological sample, a measure of aggregation of the analyte in the biological sample, a measure of purity or integrity of the analyte in the biological sample, and a concentration of the analyte in the biological sample. The first chromatography column can be a cation exchange chromatography column, the second chromatography column can be a size exclusion chromatography column, and the third chromatography column can be a reversed phase chromatography column.

The sample purification device can include an affinity chromatography column. The analyte can include a protein in the biological sample. The protein can include an antibody in the biological sample.

The systems can include a column manager in fluid communication with the first, second, and third sample analyzers and with the second flow control device, and coupled to the control unit, where the control unit is configured to adjust a configuration of the column manager to direct the portion of the biological sample into one of the first, second, and third sample analyzers. The systems can include a sampling device coupled to the control unit and configured to receive the biological sample, and to deliver the portion of the biological sample to the first fluid control device.

The quantification detector can include one of a diode array detector, a spectrometric detector configured to measure absorbance information for the portion of the biological sample, a fluorescence detector, and a mass spectrometric detector.

Embodiments of the systems can also include any of the other features described herein, including any combinations of features individually disclosed in different embodiments, except as expressly stated otherwise.

In a further aspect, the disclosure features methods for measuring product quality attributes of an analyte of a biological sample, the methods including obtaining a biological sample by extracting the biological sample from an operating bioreactor or from a purification apparatus in fluid communication with the operating bioreactor, directing a first portion of the biological sample to a first sample analyzer and obtaining information about a first product quality attribute of an analyte of the biological sample by analyzing the first portion of the biological sample in the first sample analyzer, directing a second portion of the biological sample to a second sample analyzer and obtaining information about a second product quality attribute of an analyte of the biological sample by analyzing the second portion of the biological sample in the second sample analyzer, where the first and second product quality attributes are different, and where at least one of the first and second product quality attributes includes a measure of charge variants or heterogeneity of the analyte in the biological sample, a measure of aggregation of the analyte in the biological sample, a measure of purity or integrity of the analyte in the biological sample, and a concentration of the analyte in the biological sample.

Embodiments of the methods can also include any of the other features described herein, including any combinations of features individually disclosed in different embodiments, except as expressly stated otherwise.

Definitions

The term "unit operation" is a term of art and means a functional step that can be performed in a process of manufacturing a therapeutic protein drug substance from a liquid culture medium. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant therapeutic protein, and removing unwanted salts.

The term "cycle of chromatography" or "chromatography cycle" is a term of art and means all the steps performed in a single round of chromatography using a single chromatography column. For example, a cycle of chromatography can include a step of equilibrating a chromatography column with a buffer, passing a sample including a recombinant protein through the chromatography column, eluting the recombinant protein from the chromatography column, and washing the chromatography column by passing a denaturing buffer through the column. Additional examples of steps performed in a cycle of chromatography are described herein. Further examples of steps performed in a cycle of chromatography are also well known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant therapeutic protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant therapeutic protein (e.g., through the use of affinity chromatography). Non-limiting methods for capturing a recombinant therapeutic protein from a liquid culture medium or diluted liquid culture medium are described herein and others are known in the art. A recombinant therapeutic protein can be captured from a liquid culture medium using at least one chromatography column and/or chromatographic membrane (e.g., any of the chromatography columns and/or chromatographic membranes described herein).

The term "purifying" means a step performed to isolate a recombinant therapeutic protein from one or more other impurities (e.g., bulk impurities) or components present in a fluid containing a recombinant therapeutic protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a resin, membrane, or any other solid support that binds either a recombinant therapeutic protein or contaminants (e.g., through the use of affinity chromatography, hydrophobic interaction chromatography, anion or cation exchange chromatography, or molecular sieve chromatography). A recombinant therapeutic protein can be purified from a fluid containing the recombinant therapeutic protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant therapeutic protein that is close to a final desired purity. For example, polishing can be performed by passing a fluid containing the recombinant therapeutic protein through a chromatographic column(s) or membrane absorber(s) that selectively binds to either the target recombinant therapeutic protein or small amounts of contaminants or impurities present in a fluid containing a recombinant therapeutic protein. In such an example, the eluate/filtrate of the chromatographic column(s) or membrane absorber(s) contains the recombinant therapeutic protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "eluate/filtrate" is a term of art and means a fluid that is emitted from a chromatography column or chromatographic membrane that contains a detectable amount of a recombinant therapeutic protein.

The term "isolate" or "isolating" in certain contexts means at least partially purifying or purifying (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a recombinant protein from one or more other components present in the filtrate (e.g., a filtrate generated using the presently described methods), for example one or more components of DNA, RNA, and/or other proteins present in the filtrate. Non-limiting methods for isolating a protein from a filtrate are described herein and others are known in the art.

The term "integrated process" means a process which is performed using structural elements that function cooperatively to achieve a specific result (e.g., the generation of a therapeutic protein drug substance from a liquid culture medium).

The term "continuous process" means a process which continuously feeds fluid through at least a part of the system. For example, in any of the exemplary continuous biological manufacturing systems described herein, a liquid culture medium containing a recombinant therapeutic protein is continuously fed into the system while it is in operation and a therapeutic protein drug substance is fed out of the system. In another example, a continuous process is a process which continuously feeds a liquid culture medium containing a recombinant therapeutic protein from a bioreactor through a first MCCS. Another example of a continuous process is a process which continuously feeds a liquid culture medium containing a recombinant therapeutic protein from a bioreactor through a first and second MCCS. Additional examples include a process which continuously feeds a liquid culture medium containing a recombinant therapeutic protein through a first MCCS, a process that continuously feeds a liquid culture medium containing a recombinant therapeutic protein through a first and second MCCS, or a process that continuously feeds a fluid containing a recombinant therapeutic protein through a second MCCS.

The term "biological manufacturing system" or "bio-manufacturing system" refers to system for producing a biological drug.

The term "biological drug" means any therapeutic substance made or obtained from a living organism or its products that is used in the prevention, diagnosis or treatment of a pathology. Thus, a biological drug or biopharmaceutical is a medical drug produced using biotechnology, for example, a protein (e.g., a recombinant therapeutic protein), or a nucleic acid (DNA, RNA, or antisense oligonucleotides), used for therapeutic or in vivo diagnostic purposes.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "mammalian cell" means any cell from or derived from any mammal (e.g., a human, a hamster, a mouse, a green monkey, a rat, a pig, a cow, or a rabbit). In some embodiments, the mammalian cell can be, e.g., an immortalized cell, a differentiated cell, or an undifferentiated cell.

The term "cell culture" means a plurality of mammalian cells (e.g., any of the mammalian cells described herein) suspended in a liquid culture medium (e.g., any of the liquid culture media described herein). The cell culture can have a cell density of greater than about $0.1 \times 10^6$ cells/mL (e.g., greater than about $1.0 \times 10^6$ cells/mL, greater than about $5.0 \times 10^6$ cells/mL, greater than about $10 \times 10^6$ cells/mL, greater than about $15 \times 10^6$ cells/mL, greater than about $20 \times 10^6$ cells/mL, greater than about $25 \times 10^6$ cells/mL, greater than about $30 \times 10^6$ cells/mL, greater than about $35 \times 10^6$ cells/mL, greater than about $40 \times 10^6$ cells/mL, greater than about $45\times10^6$ cells/mL, greater than about $50\times10^6$ cells/mL, greater than about $55\times10^6$ cells/mL, greater than about $60\times10^6$ cells/mL, greater than about $65\times10^6$ cells/mL, greater than about $70\times10^6$ cells/mL, greater than about $75\times10^6$ cells/mL, greater than about $80\times10^6$ cells/mL, greater than about $85\times10^6$ cells/mL, greater than about $90\times10^6$ cells/mL, greater than about $95\times10^6$ cells/mL, or greater than about $100\times10^6$ cells/mL).

The term "culturing" or "cell culturing" means the maintenance or growth of a mammalian cell in a liquid culture medium under a controlled set of physical conditions.

The term "liquid culture medium" means a fluid that contains sufficient nutrients to allow a mammalian cell to grow in the medium in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, ion, copper, zinc, selenium, and other necessary trace metals, and sodium bicarbonate. A liquid culture medium may contain serum from a mammal. In some instances, a liquid culture medium does not contain serum or another extract from a mammal a defined liquid culture medium). A liquid culture medium may contain trace metals, a mammalian growth hormone, and/or a mammalian growth factor. Non-limiting examples of liquid culture medium are described herein and additional examples are known in the art and are commercially available.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')2 fragment, or an scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "recombinant therapeutic protein" or "recombinant protein" refers to any therapeutic protein obtained via recombinant DNA technology. As used herein, a "recombinant therapeutic protein" includes, for example, an antibody or antibody fragment, an enzyme, an engineered protein, or an immunogenic protein or protein fragment.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). A "secreted" protein need not dissociate entirely from the cell to be considered a secreted protein.

The term "perfusion bioreactor" means a bioreactor containing a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like symbols in the drawings indicate like elements.

DETAILED DESCRIPTION

Introduction

Industrial scale bio-manufacturing can be performed in two-column and multi-column chromatography systems in a variety of configurations. In these complex systems, product yield, quality, and waste rates are functions of a large number of process-related parameters and steps. During manufacturing of therapeutic proteins and other commercially valuable bio-molecules, product outcomes can be strongly influenced by these parameters and steps. Appropriate control over such parameters and steps is therefore an important aspect of large scale manufacturing. Features and aspects of bio-manufacturing systems are disclosed, for example, in PCT Patent Application Publication No. WO 2014/137903, the entire contents of which are incorporated herein by reference.

Exercising appropriate control over bio-manufacturing parameters, including automated control, is facilitated by monitoring of bioreactor harvest, intermediate solution streams, and/or products. Conventional monitoring techniques include, for example, UV absorbance measurements.

Unfortunately, such methods can be subject to drift over measurement periods of a few days due to factors such as temperature, humidity, ambient light intensities, and local sample inhomogeneity. Furthermore, such methods may not allow multiple quantities to be calculated or otherwise determined. In complex bio-manufacturing environments, multiple quantities are generally assessed to provide suitable feedback information for adjustment of process parameters.

This disclosure features systems and methods that can be used to determine values of multiple product quality attributes. The systems can be implemented as two-dimensional chromatography systems. Along a first dimension of the system, a portion of a biological sample can optionally be purified using a sample purification device, which can include a chromatography column. Along a second dimension of the system, the portion of the sample can then be directed to one of multiple different sample analyzers to determine a product quality attribute for the sample. Additional portions of the sample can be directed to different sample analyzers to determine different product quality attributes for the sample.

Product Quality Attribute Analysis Systems

Figure 1:
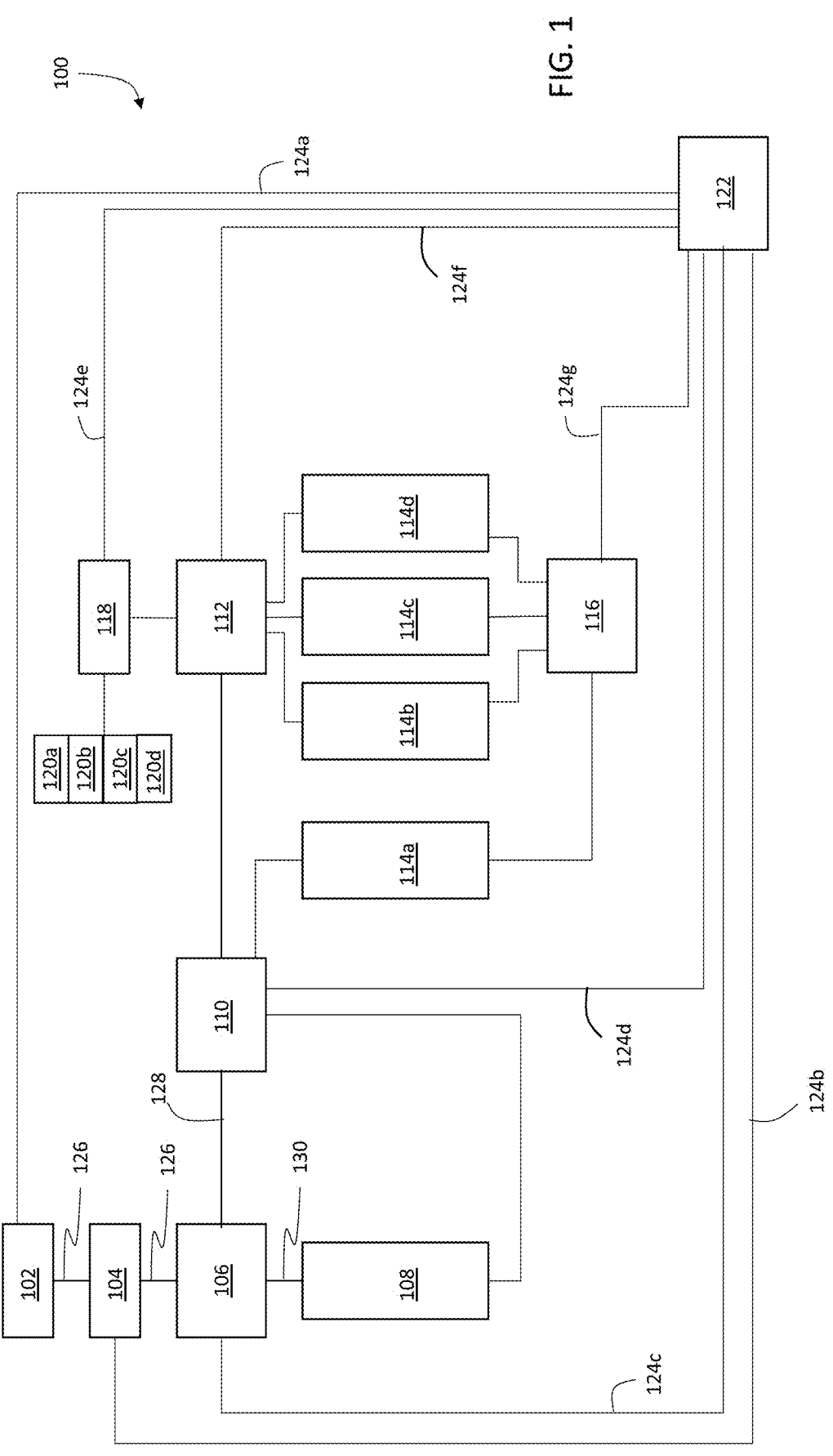
FIG. 1 is a schematic diagram of an example of a system for determining product quality attributes for an analyte of a biological sample.

FIG. 1 is a schematic diagram showing an example of a measurement system 100 for measuring multiple product quality attributes. System 100 includes a sample manager 102, a first pump 104 (e.g., a binary pump), a first flow control device 106, a sample purification device 108, a second flow control device 110, a column manager 112, multiple sample analyzers 114a-114d, a detector 116, a second pump 118 (e.g., a quaternary pump), solvent/buffer reservoirs 120a-120d, and a control unit 122. Sample manager 102, pump 104, first flow control device 106, second flow control device 110, column manager 112, and detector 116 can be coupled to control unit 122 via communication lines 124a-124g.

During operation, sample manager 102 receives a biological sample for analysis. Sample manager 102 can be implemented in various ways. In some embodiments, for example, sample manager includes a container receiver configured to receive a sample in a container. Suitable containers include, for example, vials, tubes, and other sealed or unsealed vessels. In certain embodiments, samples can be carried by single- or multi-well plates, and container receiver is configured to receive such plates. Sample manager 102 can optionally include a transfer mechanism for transferring portions of the biological sample into first flow control device 106. Suitable transfer mechanisms include, but are not limited to, syringe-based sample injection devices, and single- or multi-channel fluid transfer devices. Examples of suitable sample managers include the Waters H Class Sample Manager with Flow Through Needle, and the Waters Process Sample Manager (both available from Waters Corp., Milford, MA).

In certain embodiments, sample manager 102 receives a biological sample from a sampling device in fluid communication with a bioreactor, a fluid conduit, or another component of a biological manufacturing system. For example, the biological sample can be harvested directly from a bioreactor (and therefore corresponds to a harvested sample of growth medium), or can be a solution or medium extracted from another location in the biological manufacturing system.

Figure 2:
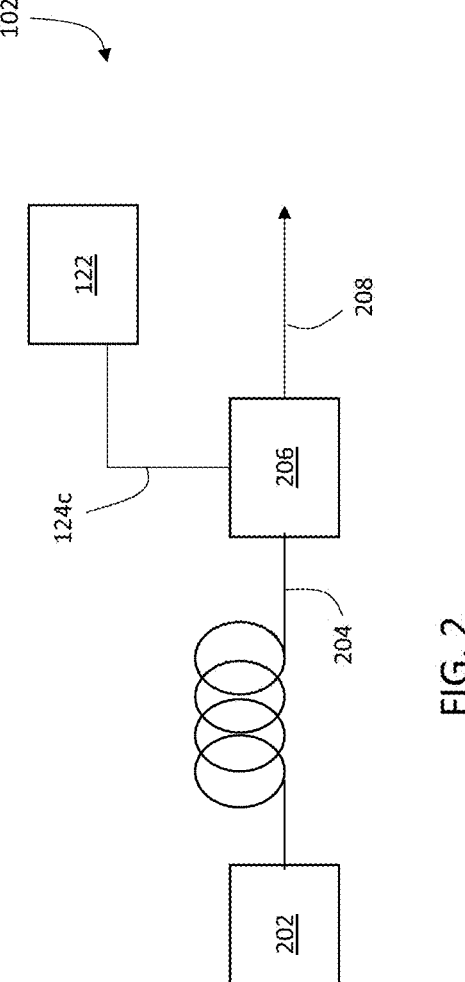
FIG. 2 is a schematic diagram of an example of a sample manager.

FIG. 2 is a schematic diagram of an example of a sample manager 102 that is configured to receive a biological sample directly from a sampling device. Sample manager 102 includes an inlet 202, a holding conduit 204, and a gate valve 206 coupled to control unit 122 via control line 124c. The biological sample is introduced into sample manager 102 through inlet 202, and the sample is maintained prior to delivery into first flow control device 106 within holding conduit 204. To deliver a portion of the sample into first flow control device 106, control unit 122 transmits a signal to gate valve 206. Gate valve 206 opens, discharging a portion of the sample from holding conduit 204 into outlet conduit 208. The discharged portion of the sample is then pumped (e.g., by first pump 104) to first flow control device 106.

In general, a wide variety of different biological samples can be received by sample manager 102. In some embodiments, as described above, the biological sample corresponds to a harvested portion of a growth medium from a bio-reactor. In certain embodiments, the biological sample corresponds to a process fluid or medium extracted from another location in a biological manufacturing system, such as a product- or intermediate-containing solution sampled before or after a purification stage in the biological manufacturing system.

In certain embodiments, system 100 can be used to determine product quality attributes for cell line development, and the biological sample corresponds to a portion of a cell culture, a cell culture medium, a fluidic suspension of cells, or another type of sample in which cells, cellular breakdown products, cellular metabolites, and/or cell culture impurities are present.

System 100 determines product quality attributes for one or more analytes in the biological sample that is received by sample manager 102. In general, attributes can be determined for a wide variety of different types of analytes. For example, in some embodiments, system 100 determines product quality attributes for protein analytes including, but not limited to, antibodies (including mono-, bi-, and tri-specific antibodies), non-antibody proteins, fusion proteins, and/or Fab fragments.

In some embodiments, the analyte is a recombinant therapeutic protein. Non-limiting examples of recombinant therapeutic proteins that can be analyzed using the systems and method disclosed herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., Current Opin. Chem. Biol. 13:245-255, 2009; and U.S. Patent Application Publication No. 2012/0164066 (herein incorporated by reference in its entirety)).

Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab.

Additional non-limiting examples of recombinant therapeutic proteins that can be analyzed include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factov VIII, factor VIIa, anti-thrombin III, protein C, human albumin, erythropoietin, granulocute colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Additional examples of recombinant proteins that can be produced by the present methods include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

As discussed above, in some embodiments, the analyte is a component of a cell, and the methods and systems described herein can be used for cell line process development. Examples of such cells include, but are not limited to, bacteria (e.g., gram negative bacteria), yeast (e.g., *Saccharomyces cerevisiae, Pichia pastoris, Hansenula polymorpha, Kluyveromyces lactis, Schizosaccharomyces pombe, Yarrowia lipolytica*, or *Arxula adeninivorans*), or mammalian cells. The mammalian cell can be a cell that grows in suspension or an adherent cell. Non-limiting examples of mammalian cells include: Chinese hamster ovary (CHO) cells (e.g., CHO DG44 cells or CHO-K1s cells), Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells.

The mammalian cell can contain a recombinant nucleic acid (e.g., a nucleic acid stably integrated in the mammalian cell's genome) that encodes a recombinant therapeutic protein. Non-limiting examples of recombinant nucleic acids that encode exemplary recombinant therapeutic proteins are described below, as are recombinant therapeutic proteins that can be produced using the methods described herein. In some instances, the mammalian cell that is cultured in a bioreactor (e.g., any of the bioreactors described herein) was derived from a larger culture.

A nucleic acid encoding a recombinant therapeutic protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant therapeutic protein is not stably integrated into a chromosome of the mammalian cell (transient transfection), while in others the nucleic acid is integrated. Alternatively or in addition, the nucleic acid encoding a recombinant therapeutic protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some embodiments, the recombinant therapeutic protein is a secreted protein and is released by the mammalian cell into the extracellular medium. For example, a nucleic acid sequence encoding a soluble recombinant therapeutic protein can contain a sequence that encodes a secretion signal peptide at the N- or C-terminus of the recombinant therapeutic protein, which is cleaved by an enzyme present in the mammalian cell, and subsequently released into the extracellular medium.

After the biological sample is received by sample manager 102, the sample is transported by first pump 104 through conduit 126 to first flow control device 106. First flow control device 106 is connected to control unit 122 via control line 124*b*. In general, the biological sample can be delivered to multiple different outputs by first flow control device 106. In a first configuration, first flow control device 106 delivers the biological sample directly to second flow control device 110 via conduit 128. In another configuration, first flow control device 106 delivers the biological sample to a sample purification device 108 via conduit 130. Control unit 122 is configured to adjust the configuration of first flow control device 106 to direct the biological sample to either destination, depending upon the desired mode of analysis of the biological sample.

First flow control device 106 can be implemented in various ways. In some embodiments, for example, first flow control device 106 can be implemented as a multi-way valve. Suitable valves include, for example, the IDEX MX Series II 2-position, 6-port UltraLife Switching valve (available from IDEX Corp., Lake Forest, IL). In certain embodiments, first flow control device 106 can be implemented as a multi-channel fluidic device with input and/or output manifolds and electrically controllable flow regulators.

When the biological sample is directed to sample purification device 108, the biological sample is at least partially purified prior to analyzing the sample in system 100. Purification can occur in various ways, but typically involves removing one or more non-analyte components from the sample. Alternatively, or in addition, purification of the biological sample can also include concentration of an analyte in the sample, and separation of one analyte from one or more additional analytes in the sample.

Sample purification device 108 can be implemented in various ways. In some embodiments, for example, sample purification device 108 is implemented as a chromatography apparatus and features one or more chromatography columns. Suitable chromatography columns for use in sample purification device 108 include, for example, affinity chromatography columns. The term "affinity chromatography" refers to a type of chromatography where an analyte molecule (e.g., a recombinant protein analyte) is captured and isolated based on affinity. Affinity chromatography refers to the use of an affinity chromatography resin (e.g., an affinity chromatography resin including a protein ligand (e.g., protein A or protein G)). In some embodiments, affinity chromatography include a pseudo-affinity chromatography resin. In some embodiments, an affinity chromatography resin includes a cofactor ligand, a substrate ligand, a metal ligand, a product ligand, or an aptamer ligand. In general, the affinity chromatography resin can include any receptor or ligand having an affinity for any biological analyte, including DNA, oligonucleotides. In some embodiments, the affinity chromatography resin can include single-domain antibody fragments from the family Camelidae. for the purification of gene therapy vectors. As another example, the affinity chromatography column can be an adeno-associated virus (AAV) affinity chromatography column.

Non-limiting examples of an affinity chromatography resin can include a protein or peptide ligand (e.g., between about 5 amino acids to about 100 amino acids, between about 5 amino acids to about 90 amino acids, between about 5 amino acids to about 80 amino acids, between about 5 amino acids to about 70 amino acids, between about 5 amino acids to about 60 amino acids, between about 5 amino acids to about 50 amino acids, between about 5 amino acids to about 40 amino acids, between about 5 amino acids to about 30 amino acids, or between about 5 amino acids to about 20 amino acids), a small molecule substrate or cofactor of an enzyme, an aptamer, an inhibitor (e.g., a competitive protein inhibitor) or a metal.

Non-limiting examples of protein A affinity chromatography resins are: GE MabSelect SuRe™ (a highly cross-linked agarose resin having a particle size of 85 μm, and epoxy functional groups connecting protein A to the agarose), JSR LifeSciences Amsphere ProA JWT203 (a porous poly-methacrylate resin having a particle size of ~50 μm, and epoxy functional groups connecting protein A to the poly-methacrylate), and Kaneka KanCap A (a highly cross-linked cellulose having a particle size of 65-85 μm, with protein A linked to the cellulose through reductive amination).

For an affinity chromatography column, e.g., a protein A column, the steps in a cycle of affinity chromatography can include the steps of loading an affinity column, e.g., a protein A chromatography column, with a fluid including the analyte, washing the column to remove unwanted biological material (e.g., contaminating proteins and/or small molecules), eluting the target recombinant protein bound to the column, and re-equilibrating the column.

Any of the single steps in a chromatography cycle can include a single buffer or multiple buffers (e.g., two or more buffers), and one or more of any of the single steps in a chromatography cycle can include a buffer gradient. Any of the combination of various well-known aspects of a single cycle of chromatography can be used in these methods in any combination, e.g., different chromatography resin(s), flow-rate(s), buffer(s), void volume(s) of the column, bed volume(s) of the column, volume(s) of buffer used in each step, volume(s) of the fluid including the target protein, and the number and types of buffer(s) used in each step.

In some embodiments, the protein A column can be loaded with 1× phosphate-buffered saline (PBS) at a pH of about 7 (e.g., about pH 7.0 about pH 7.1, about pH 7.2, about pH 7.3, about pH 7.4, about pH 7.5, about pH 7.6, about pH 7.7, about pH 7.8, or about pH 7.9). In some embodiments, the protein A column can be loaded with 1×PBS at about pH 7.2.

In some embodiments, the protein A column is eluted with a buffer including about 50 mM to about 200 mM citric acid phosphate (e.g., about 50 mM to about 190 mM, about 50 mM to about 180 mM, about 50 mM to about 170 mM, about 50 mM to about 160 mM, about 50 mM to about 150 mM, about 50 mM to about 140 mM, about 50 mM to about 130 mM, about 50 mM to about 120 mM, about 50 mM to about 110 mM, about 50 mM to about 100 mM, about 50 mM to about 90 mM, about 50 mM to about 80 mM, about 50 mM to about 70 mM, about 50 mM to about 60 mM, about 75 mM to about 200 mM, about 75 mM to about 190 mM, about 75 mM to about 180 mM, about 75 mM to about 170 mM, about 75 mM to about 160 mM, about 75 mM to about 150 mM, about 75 mM to about 140 mM, about 75 mM to about 130 mM, about 75 mM to about 120 mM, about 75 mM to about 110 mM, about 75 mM to about 100 mM, about 75 mM to about 90 mM, about 75 mM to about 80 mM, about 100 mM to about 200 mM, about 100 mM to about 190 mM, about 100 mM to about 180 mM, about 100 mM to about 170 mM, about 100 mM to about 160 mM, about 100 mM to about 150 mM, about 100 mM to about 140 mM, about 100 mM to about 130 mM, about 100 mM to about 120 mM, about 100 mM to about 110 mM, about 125 mM to about 200 mM, about 125 mM to about 190 mM, about 125 mM to about 180 mM, about 125 mM to about 170 mM, about 125 mM to about 160 mM, about 125 mM to about 150 mM, about 125 mM to about 140 mM, about 125 mM to about 130 mM, about 150 mM to about 200 mM, about 150 mM to about 190 mM, about 150 mM to about 180 mM, about 150 mM to about 170 mM, about 150 mM to about 160 mM, about 175 mM to about 200 mM, about 175 mM to about 190 mM, about 175 mM to about 180 mM, or about 180 mM to about 200 mM), about 50 mM to about 200 mM NaCL (e.g., about 50 mM to about 190 mM, about 50 mM to about 180 mM, about 50 mM to about 170 mM, about 50 mM to about 160 mM, about 50 mM to about 150 mM, about 50 mM to about 140 mM, about 50 mM to about 130 mM, about 50 mM to about 120 mM, about 50 mM to about 110 mM, about 50 mM to about 100 mM, about 50 mM to about 90 mM, about 50 mM to about 80 mM, about 50 mM to about 70 mM, about 50 mM to about 60 mM, about 75 mM to about 200 mM, about 75 mM to about 190 mM, about 75 mM to about 180 mM, about 75 mM to about 170 mM, about 75 mM to about 160 mM, about 75 mM to about 150 mM, about 75 mM to about 140 mM, about 75 mM to about 130 mM, about 75 mM to about 120 mM, about 75 mM to about 110 mM, about 75 mM to about 100 mM, about 75 mM to about 90 mM, about 75 mM to about 80 mM, about 100 mM to about 200 mM, about 100 mM to about 190 mM, about 100 mM to about 180 mM, about 100 mM to about 170 mM, about 100 mM to about 160 mM, about 100 mM to about 150 mM, about 100 mM to about 140 mM, about 100 mM to about 130 mM, about 100 mM to about 120 mM, about 100 mM to about 110 mM, about 125 mM to about 200 mM, about 125 mM to about 190 mM, about 125 mM to about 180 mM, about 125 mM to about 170 mM, about 125 mM to about 160 mM, about 125 mM to about 150 mM, about 125 mM to about 140 mM, about 125 mM to about 130 mM, about 130 mM to about 200 mM, about 130 mM to about 190 mM, about 130 mM to about 180 mM, about 130 mM to about 170 mM, about 130 mM to about 160 mM, about 130 mM to about 150 mM, about 140 mM to about 200 mM, about 140 mM to about 190 mM, about 140 mM to about 180 mM, about 140 mM to about 170 mM, about 140 mM to about 160 mM, about 140 mM to about 150 mM, about 150 mM to about 200 mM, about 150 mM to about 190 mM, about 150 mM to about 180 mM, about 150 mM to about 170 mM, about 150 mM to about 160 mM, about 175 mM to about 200 mM, about 175 mM to about 190 mM, about 175 mM to about 180 mM, or about 180 mM to about 200 mM), at about pH 2 to about pH 4 (e.g., about pH 2 to about pH 3.8, about pH 2 to about pH 3.6, about pH 2 to about pH 3.8, about pH 2 to about pH 3.6, about pH 2 to about pH 3.4, about pH 2 to about pH 3.2, about pH 2 to about pH 3.0, about pH 2 to about pH 2.8, about pH 2 to about pH 2.6, about pH 2 to about 2.4, about pH 2 to about pH 2.2, about pH 3 to about pH 4, about pH 3 to about pH 3.8, about pH 3 to about pH 3.6, about pH 3 to about pH 3.4, or about pH 3 to about pH 3.2).

In some embodiments, the protein A column is eluted with about 10 mM to about 100 mM (e.g., 10 mM to about 90 mM, about 10 mM to about 80 mM, about 10 mM to about 70 mM, about 10 mM to about 60 mM, about 10 mM to about 50 mM, about 10 mM to about 40 mM, about 10 mM to about 30 mM, about 10 mM to about 20 mM, about 15 mM to about 100 mM, about 15 mM to about 90 mM, about 15 mM to about 80 mM, about 15 mM to about 70 mM, about 15 mM to about 60 mM, about 15 mM to about 50 mM, about 15 mM to about 40 mM, about 15 mM to about 30 mM, about 15 mM to about 20 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 40 mM, about 20 mM to about 30 mM, about 20 mM to about 25 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 50 mM to about 100 mM, about 50 mM to about 90 mM, about 50 mM to about 80 mM, about 50 mM to about 70 mM, about 50 mM to about 60 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 100 mM, about 80 mM to about 90 mM, or about 90 mM to about 100 mM) sodium acetate, at about pH 2 to about pH 4 (e.g., about pH 2 to about pH 3.8, about pH 2 to about 3.75, about pH 2 to about pH 3.6, about pH 2 to about pH 3.8, about pH 2 to about pH 3.6, about pH 2 to about pH 3.4, about pH 2 to about pH 3.2, about pH 2 to about pH 3.0, about pH 2 to about pH 2.8, about pH 2 to about pH 2.6, about pH 2 to about 2.4, about pH 2 to about pH 2.2, about pH 3 to about pH 4, about pH 3 to about pH 3.8, about pH 3 to about pH 3.75, about pH 3 to about pH 3.6, about pH 3 to about pH 3.4, or about pH 3 to about pH 3.2).

Chromatography performed using this type of chromatography column can include, e.g., the sequential chromatographic steps of loading, washing, eluting, and regenerating the chromatography column are generally performed. Any of the exemplary flow rates, buffer volumes, and/or lengths of time allotted for each sequential chromatographic step described herein can be used in any of these different sequential chromatographic steps.

In some embodiments, a single chromatographic column or single chromatographic membrane containing a resin that is capable of capturing the analyte is loaded in, e.g., between about 5 minutes to about 90 minutes (e.g., between about 10 minutes and about 90 minutes, between about 15 minutes and 80 minutes, between about 20 minutes and 80 minutes, between about 30 minutes and about 80 minutes, between about 40 minutes and about 80 minutes, and between about 50 minutes and 80 minutes).

Following the loading of the analyte onto the column, the column is washed with at least one washing buffer. The at least one (e.g., two, three, or four) washing buffer(s) is/are meant to elute all compounds that are not the analyte from the column, while not disturbing the interaction of the analyte with the resin.

The washing buffer can be passed through the column at a flow rate of between about 0.1 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute).

The volume of washing buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, or between about 30 minutes to about 1 hour).

Following the washing of the column, the analyte is eluted from the column by passing an elution buffer through the column. The elution buffer can be passed through the column at a flow rate of between about 0.2 mL/minute to about 25 mL/minute (e.g., between about 0.1 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 1.0 mL/minute and about 15.0 mL/minute). The volume of elution buffer used to elute the analyte from the column can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 0.1 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes, between about 0.1 minutes and about 10 minutes).

Non-limiting examples of elution buffers that can be used depend on the capture mechanism and/or the analyte. For example, an elution buffer can contain a different concentration of salt (e.g., increased salt concentration), a different pH (e.g., an increased or decreased salt concentration), or a molecule that will compete with the analyte for binding to the resin. Examples of such elution buffers are described above.

Following the elution of the analyte from the column, the column can be equilibrated using a regeneration buffer. The regeneration buffer can be passed through the column at a flow rate of, e.g., between about 0.1 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute).

The volume of regeneration buffer used to equilibrate the column can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 2×CV to about 5×CV, about 4×CV to about 11×CV, about 5×CV to about 11×CV, or about 5×CV to about 10×CV).

In some embodiments, sample purification device 108 includes a single affinity chromatography column. In certain embodiments, sample purification device 108 includes multiple affinity chromatography columns. Where multiple columns are used, the columns can be different (e.g., include different chromatography resins), or can be the same. Further, the multiple columns can be loaded and/or eluted with the same solvents and buffers, or with different solvents and/or buffers. Each of the columns in a multi-column sample purification device can include any one or more of the chromatography resins described herein, and can be loaded and/or eluted with any one or more of the different solvents and buffers described herein.

The biological sample is delivered to second flow control device 110 either directly from first flow control device 106, or via sample purification device 108, as described above. Second flow control device 110 receives the biological sample and directs it along one of multiple flow paths according to a control signal from control unit 122 transmitted on control line 124d. Second flow control device 110 can generally be implemented in the same manner as first flow control device 106 described above.

In general, second flow control device 110 directs the biological sample to one of multiple sample analyzers as shown in FIG. 1. In general, system 100 can include 2 or more sample analyzers (e.g., 3 or more, 4 or more, 5 or more, 6 or more, 7 or more, 8 or more, 10 or more, 15 or more, or even more). Each of the sample analyzers is associated with the measurement of one product quality attribute for an analyte of the biological sample. In FIG. 1, four different sample analyzers 114a-114d are shown by way of example. However, it should be understood that system 100 can include any number of sample analyzers, depending upon the number of product quality attributes to be measured.

In some embodiments, a particular sample analyzer does not include a chromatography column. For example, in FIG. 1, sample analyzer 114a does not include a chromatography column. The biological sample can be delivered directly to sample analyzer 114a from second flow control device 110. More specifically, when the product quality attribute associated with sample analyzer 114a is to be measured, control unit 122 transmits a control signal to second flow control device 110, adjusting the configuration of second flow control device 110 and causing the biological sample to be delivered to sample analyzer 114a. The product quality attribute associated sample analyzer 114a is measured for an analyte in the biological sample.

In certain embodiments, a particular sample analyzer includes a chromatography column. For example, in FIG. 1, sample analyzers 114b-114d each include a chromatography column. To deliver a biological sample to such a sample analyzer, the sample can be delivered directly from second flow control device 110 under the control of control unit 122, as described above.

Alternatively, in some embodiments, system 100 optionally includes a column manager 112 that receives the biological sample from second flow control device 110 and directs it into the sample analyzer. A column manager can be particularly useful in systems that include multiple sample analyzers with chromatography columns. As shown in FIG. 1, column manager 112 can be coupled to control unit 122 via control line 124f To direct the biological sample into a sample analyzer associated with a particular product quality attribute to be measured, control unit 122 can transmit a control signal to column manager 112, adjusting the configuration of the column manager 112 to direct the biological sample into a flow path of the sample analyzer.

Column manager 112 can optionally be in fluid communication with one or more reservoirs (shown in FIG. 1 as four reservoirs 120a-120d for illustrative purposes) via a second pump 118, which can also be optionally coupled to control unit 122 via control line 124e. When the biological sample is directed into a particular sample analyzer, control unit 122 also transmits a control signal to second pump 118, causing second pump 118 to direct a flow of a suitable loading buffer, elution buffer, or other suitable solvent or solution into the particular sample analyzer. Although four reservoirs are shown by way of example in FIG. 1, it should generally be understood that second pump 118 can be in fluid communication with 2 or more reservoirs (e.g., 3 or more, 4 or more, 5 or more, 6 or more, 8 or more, 10 or more, 15 or more, 20 or more, or even more).

Second pump can generally be implemented in a variety of ways. For example, in some embodiments, a suitable second pump 118 is the Waters H-Class Bio Quaternary Pump with an additional solvent select valve modification (Waters Corp., Milford, MA).

After the biological sample has been loaded onto the column of a selected chromatographic sample analyzer, the column is developed and eluted, and the eluate is analyzed to provide information about the product quality attribute associated with the sample analyzer for an analyte of the biological sample.

Analysis of the eluate can be performed in a variety of ways. In some embodiments, for example, system 100 includes a detector 116 in fluid communication with the outlet of a sample analyzer's chromatography column. Detector 116 detects the analyte in the eluate, and provides measurement information via control line 124g to control unit 122. Control unit 122 uses the measurement information (which generally corresponds to chromatograms and/or chromatographic information such as detected peak heights, areas, and times) to determine a value of a particular product quality attribute for an analyte of the biological sample.

System 100 can generally use a wide variety of detectors. In some embodiments, detector 116 corresponds to a photodiode array detector. Suitable diode array detectors for use in system 100 include, but are not limited to, the Waters Photodiode Array Detector (Waters Corp., Milford, MA).

Other types of detectors can also be used. For example, in some embodiments, detector 116 corresponds to an absorption spectrometer that measures absorbance of the biological sample (e.g., in at least one of the ultraviolet, visible, and infrared regions of the electromagnetic spectrum). In certain embodiments, detector 116 can be implemented as a fluorescence detector, and includes a light source for directing illumination light onto the biological sample, and a detection element for measuring fluorescence emission from the sample. In some embodiments, detector 116 can be implemented as a mass spectrometry detector in which the biological sample is ionized and the distribution of ions is resolved by mass to determine abundance information for the biological sample. In certain embodiments, detector 116 can be implemented as a multi-angle light scattering detector, or an angle-of-refraction detector.

In some embodiments, each column-based sample analyzer can be in fluid communication with a different, dedicated detector. In certain embodiments, as shown in FIG. 1, two or more column-based sample analyzers can be in fluid communication with a common detector. That is, detector 116 can be shared between two or more sample analyzers, as system 100 analyzes only one portion of a biological sample at a time.

In some embodiments, detector 116 functions effectively as a sample analyzer. For example, in FIG. 1, sample analyzer 114a can include a fluid conduit extending between second flow control device 110 and detector 116. When a sample is delivered into sample analyzer 114a, the sample simply propagates through the fluid conduit, and is subsequently analyzed directly by detector 116.

In general within system 100, each sample analyzer is dedicated to the measurement of a particular product quality attribute for an analyte in a biological sample. The particular product quality attribute to be determined is selected by control unit 122, which adjusts the configuration of second flow control device 110 to direct a portion of the biological sample to one of the sample analyzers.

System 100 can generally be configured to measure any number of product quality attributes, depending upon the number of sample analyzers present in the system. For example, in certain embodiments, system 100 can measure 2 or more (e.g., 3 or more, 4 or more, 5 or more, 6 or more, 7 or more, 8 or more, 10 or more, 12 or more, 15 or more, 20 or more, or even more) product quality attributes for an analyte in a biological sample.

Product Quality Attributes

As discussed above, system 100 can be used to measure multiple product quality attributes for an analyte in a biological sample. A variety of product quality attributes can be measured, depending upon the nature of the sample analyzers that are present in system 100.

(a) Concentration or Titer

In some embodiments, system 100 includes a sample analyzer that measures concentration or titer of an analyte in a biological sample. Concentration or titer of an analyte can be measured directly in a biological sample by any of the different types of detectors described above. Thus, for example, to measure concentration or titer for a biological sample in FIG. 1, a portion of the biological sample can be delivered directly from second flow control device 110 to detector 116, i.e., the sample analyzer can effectively be a fluid conduit extending between second flow control device 110 and detector 116.

(b) Charge Variants or Heterogeneity

In some embodiments, system 100 includes a sample analyzer that measures charge variants or heterogeneity for an analyte in a biological sample. Charge variants/heterogeneity can be determined, for example, by a sample analyzer that includes a cation exchange column for performing cation exchange chromatography of the analyte in the sample.

The term "cation exchange chromatography" refers to a type of ion exchange chromatography that uses a negatively charged ion exchange resin to separate molecules based on charge differences. In some embodiments, the cation exchange chromatography column is a strong cation exchange chromatography column, e.g., HiTrap SP HP cation exchange chromatography column, Mono S cation exchange chromatography column, Thermo MAbPac strong cation exchange chromatography column.

A cycle of chromatography using a cation exchange chromatography column (e.g., a strong cation exchange chromatography column), where the analyte binds to the chromatography resin in the loading step, can include the steps of loading the column with a fluid including the analyte, washing the column to remove unwanted biological material, eluting the analyte bound to the column, and re-equilibrating the column. In certain embodiments, a cycle of chromatography using a cation exchange chromatography column, where unwanted biological material binds to the chromatography resin during the loading step, while the analyte does not, can include the steps of loading the column with a fluid including the target protein, collecting the target recombinant protein in the flow-through, and re-equilibrating the column.

Any of the single steps in a chromatography cycle can include a single buffer or multiple buffers (e.g., two or more buffers), and one or more of any of the single steps in a chromatography cycle can include a buffer gradient. Any of the combination of various well-known aspects of a single cycle of chromatography can be used in these methods in any combination, e.g., different chromatography resin(s), flow-rate(s), buffer(s), void volume(s) of the column, bed volume(s) of the column, volume(s) of buffer used in each step, volume(s) of the fluid including the target protein, and the number and types of buffer(s) used in each step.

In some embodiments, the cation exchange column is loaded with about 50 mM to about 120 mM citric acid phosphate (e.g., about 50 mM, about 60 mM, about 70 mM, about 80 mM, about 90 mM, about 100 mM, about 110 mM, or about 120 mM), about 100 mM to about 150 mM NaCl (e.g., about 100 mM, about 110 mM, about 120 mM, about 130 mM, about 140 mM, or about 150 mM), at about pH 3 to about pH 4 (e.g., about pH 3.2, about pH 3.4, about pH 3.6, about pH 3.8, or about pH 4).

In some embodiments, the protein A column is eluted with about 10 mM to about 100 mM (e.g., 10 mM to about 90 mM, about 10 mM to about 80 mM, about 10 mM to about 70 mM, about 10 mM to about 60 mM, about 10 mM to about 50 mM, about 10 mM to about 40 mM, about 10 mM to about 30 mM, about 10 mM to about 20 mM, about 15 mM to about 100 mM, about 15 mM to about 90 mM, about 15 mM to about 80 mM, about 15 mM to about 70 mM, about 15 mM to about 60 mM, about 15 mM to about 50 mM, about 15 mM to about 40 mM, about 15 mM to about 30 mM, about 15 mM to about 20 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 40 mM, about 20 mM to about 30 mM, about 20 mM to about 25 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 50 mM to about 100 mM, about 50 mM to about 90 mM, about 50 mM to about 80 mM, about 50 mM to about 70 mM, about 50 mM to about 60 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 100 mM, about 80 mM to about 90 mM, or about 90 mM to about 100 mM) sodium acetate, at about pH 2 to about pH 4 (e.g., about pH 2 to about pH 3.8, about pH 2 to about 3.75, about pH 2 to about pH 3.6, about pH 2 to about pH 3.8, about pH 2 to about pH 3.6, about pH 2 to about pH 3.4, about pH 2 to about pH 3.2, about pH 2 to about pH 3.0, about pH 2 to about pH 2.8, about pH 2 to about pH 2.6, about pH 2 to about 2.4, about pH 2 to about pH 2.2, about pH 3 to about pH 4, about pH 3 to about pH 3.8, about pH 3 to about pH 3.75, about pH 3 to about pH 3.6, about pH 3 to about pH 3.4, or about pH 3 to about pH 3.2).

In some embodiments, the cation exchange column is eluted with about 10 mM to about 100 mM tris acetate (e.g., about 10 mM to about 90 mM, about 10 mM to about 80 mM, about 10 mM to about 70 mM, about 10 mM to about 60 mM, about 10 mM to about 50 mM, about 10 mM to about 40 mM, about 10 mM to about 30 mM, about 10 mM to about 20 mM, about 15 mM to about 100 mM, about 15 mM to about 90 mM, about 15 mM to about 80 mM, about 15 mM to about 70 mM, about 15 mM to about 60 mM, about 15 mM to about 50, about 15 mM to about 40 mM, about 15 mM to about 30 mM, about 15 mM to about 20 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 40 mM, about 20 mM to about 30 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 50 mM to about 100 mM, about 50 mM to about 90 mM, about 50 mM to about 80 mM, about 50 mM to about 70 mM, about 50 mM to about 60 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 100 mM, about 80 mM to about 90 mM, or about 90 mM to about 100 mM), and about 10 mM to about 100 mM (e.g., about 10 mM to about 90 mM, about 10 mM to about 80 mM, about 10 mM to about 70 mM, about 10 mM to about 60 mM, about 10 mM to about 50 mM, about 10 mM to about 40 mM, about 10 mM to about 30 mM, about 10 mM to about 20 mM, about 15 mM to about 100 mM, about 15 mM to about 90 mM, about 15 mM to about 80 mM, about 15 mM to about 70 mM, about 15 mM to about 60 mM, about 15 mM to about 50, about 15 mM to about 40 mM, about 15 mM to about 30 mM, about 15 mM to about 20 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 40 mM, about 20 mM to about 30 mM, about 20 mM to about 25 mM, about 25 mM to about 100 mM, about 25 mM to about 90 mM, about 25 mM to about 80 mM, about 25 mM to about 70 mM, about 25 mM to about 60 mM, about 25 mM to about 50 mM, about 25 mM to about 40 mM, about 25 mM to about 30 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 50 mM to about 100 mM, about 50 mM to about 90 mM, about 50 mM to about 80 mM, about 50 mM to about 70 mM, about 50 mM to about 60 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 100 mM, about 80 mM to about 90 mM, or about 90 mM to about 100 mM) NaCl, at about pH 7 to about pH 10 (e.g., about pH 7.2 to about pH 9.8, about pH 7.2 to about pH 9.6, about pH 7.2 to about pH 9.4, about pH 7.2 to about pH 9.2, about pH 7.2 to about pH 9, about pH 7.2 to about pH 8.8, about pH 7.2 to about pH 8.6, about pH 7.2 to about pH 8.4, about pH 7.2 to about pH 8.2, about pH 7.2 to about pH 8, about pH 7.2 to about pH 7.8, about pH 7.2 to about pH7.6, about pH 7.2 to about pH 7.4, about pH 8 to about pH 10, about pH 8 to about pH 9.8, about pH 8 to about pH 9.6, about pH 8 to about pH 9.4, about pH 8 to about pH 9.2, about pH 8 to about pH 9, about pH 8 to about pH 8.8, about pH 8 to about pH 8.6, about pH 8 to about pH 8.4, about pH 8 to about pH 8.2, about pH 9 to about pH 10, about pH 9 to about pH 9.2, about pH 9 to about pH 9.4, about pH 9 to about pH 9.6, about pH 9 to about pH 9.8, about pH 9.5 to about pH 10, or about pH 9.5 to about pH 9.8).

In some embodiments, the cation exchange column is eluted with about 10 mM to about 50 mM (e.g., 10 mM, about 20 mM, about 30 mM, about 40 mM, or about 50 mM), and about 20 mM to about 50 mM NaCl (e.g., 20 mM, about 25 mM, about 30 mM, about 40 mM, or about 50 mM), about pH 8 to about pH 10 (e.g., about pH 8 to about 9.8, about 8 to about 9.6, about pH 8 to about pH 9.4, about pH 8 to about pH 9.2, about pH 8 to about pH 9, about pH 8 to about pH 8.8, about pH 8 to about pH 8.6, about pH 8 to about pH 8.4, about pH 8 to about pH 8.2, about pH 9 to about pH 10, about pH 9 to about pH 9.8, about pH 9 to about pH 9.6, about pH 9 to about pH 9.4, about pH 9 to about pH 9.2, or about pH 9.4 to about pH 10).

(c) Aggregation

In some embodiments, system 100 includes a sample analyzer that measures aggregation of an analyte in a biological sample. The extent of aggregation can be determined, for example, by a sample analyzer that includes a size exclusion column for performing size exclusion chromatography of the analyte in the sample.

The term "size exclusion chromatography column" or "molecular sieve chromatography" refers to a chromatography column in which analytes and other components are separated by size and/or molecular weight. In some embodiments, a size exclusion chromatography column is used to separate protein aggregates, e.g., protein multimers (e.g., dimers, and trimers). Non-limiting examples of size exclusion chromatography columns include: Sephadex G-10, Sephadex G-25, Sephadex G-50, Sephadex G-75, Sephadex G-100, Sephadex G-150, Sephadex G-200, Sepharose 2B, Sepharose 4B, Sepharose 6B, Bio-gel P-300, and Waters BEH SEC 200A.

In some embodiments, a size exclusion column is loaded with 1× phosphate-buffered saline (PBS) at about pH of 7 (e.g., about pH 7.0 about pH 7.1, about pH 7.2, about pH 7.3, about pH 7.4, about pH 7.5, about pH 7.6, about pH 7.7, about pH 7.8, or about pH 7.9). In some embodiments, the size exclusion column is loaded with 1×PBS at about pH 7.2.

(d) Integrity or Purity

In some embodiments, system 100 includes a sample analyzer that measures integrity or purity of an analyte in a biological sample. The integrity or purity can be determined, for example, by a sample analyzer that includes a reversed phase column for performing reversed phase chromatography of the analyte in the sample.

The term "reversed phase chromatography" or "hydrophobic chromatography" refers to a type of chromatography that includes a hydrophobic stationary phase. Non-limiting examples of reverse phase chromatography columns are known in the art and include, e.g., Sepax Opalshell-C18. Non-limiting examples of hydrophobic ligands include aliphates, e.g., C2, C4, C8, C10, C12, C16 and C18, and polyphenyls.

A cycle of chromatography using a reversed phase chromatography column can include the steps of loading the column with a fluid including the analyte, washing the column to remove unwanted biological material, eluting the analyte bound to the column, and re-equilibrating the column.

Any of the single steps in a chromatography cycle can include a single buffer or multiple buffers (e.g., two or more buffers), and one or more of any of the single steps in a chromatography cycle can include a buffer gradient. Any of the combination of various well-known aspects of a single cycle of chromatography can be used in these methods in any combination, e.g., different chromatography resin(s), flow-rate(s), buffer(s), void volume(s) of the column, bed volume(s) of the column, volume(s) of buffer used in each step, volume(s) of the fluid including the target protein, and the number and types of buffer(s) used in each step.

In some embodiments, the reversed phase column is eluted with about 0.01% to about 1% (e.g., about 0.01% to about 0.8%, about 0.01% to about 0.6%, about 0.01% to about 0.5%, about 0.01% to about 0.4%, about 0.01% to about 0.2%, about 0.01% to about 0.1%, about 0.02% to about 1%, about 0.02% to about 0.8%, about 0.02% to about 0.6%, about 0.02% to about 0.5%, about 0.02% to about 0.4%, about 0.02% to about 0.2%, about 0.02% to about 0.1%, about 0.05% to about 1%, about 0.05% to about 0.8%, about 0.05% to about 0.6%, about 0.05% to about 0.5%, about 0.05% to about 0.4%, about 0.05% to about 0.2%, about 0.05% to about 0.1%, about 0.06% to about 1%, about 0.06% to about 0.8%, about 0.06% to about 0.6%, about 0.06% to about 0.5%, about 0.06% to about 0.4%, about 0.06% to about 0.2%, about 0.06% to about 0.1%, about 0.08% to about 1%, about 0.08% to about 0.8%, about 0.08% to about 0.6%, about 0.08% to about 0.5%, about 0.08% to about 0.4%, about 0.08% to about 0.2%, about 0.08% to about 1%, about 0.1% to about 1%, about 0.1% to about 0.8%, about 0.1% to about 0.6%, about 0.1% to about 0.5%, about 0.1% to about 0.4%, about 0.1% to about 0.2%, about 0.2% to about 1%, about 0.2% to about 0.8%, about 0.2% to about 0.6%, about 0.2% to about 0.5%, about 0.2% to about 0.4%, about 0.4% to about 1%, about 0.4% to about 0.8%, about 0.4% to about 0.6%, about 0.4% to about 0.5%, about 0.5% to about 1%, about 0.5% to about 0.8%, about 0.5% to about 0.6%, about 0.6% to about 1%, about 0.6% to about 0.8%, or about 0.8% to about 1%) trifluoroacetic acid (TFA) in water.

In some embodiments, the reversed phase column is eluted with about 0.01% to about 1% (e.g., about 0.01% to about 0.8%, about 0.01% to about 0.6%, about 0.01% to about 0.5%, about 0.01% to about 0.4%, about 0.01% to about 0.2%, about 0.01% to about 0.1%, about 0.02% to about 1%, about 0.02% to about 0.8%, about 0.02% to about 0.6%, about 0.02% to about 0.5%, about 0.02% to about 0.4%, about 0.02% to about 0.2%, about 0.02% to about 0.1%, about 0.05% to about 1%, about 0.05% to about 0.8%, about 0.05% to about 0.6%, about 0.05% to about 0.5%, about 0.05% to about 0.4%, about 0.05% to about 0.2%, about 0.05% to about 0.1%, about 0.06% to about 1%, about 0.06% to about 0.8%, about 0.06% to about 0.6%, about 0.06% to about 0.5%, about 0.06% to about 0.4%, about 0.06% to about 0.2%, about 0.06% to about 0.1%, about 0.08% to about 1%, about 0.08% to about 0.8%, about 0.08% to about 0.6%, about 0.08% to about 0.5%, about 0.08% to about 0.4%, about 0.08% to about 0.2%, about 0.08% to about 1%, about 0.1% to about 1%, about 0.1% to about 0.8%, about 0.1% to about 0.6%, about 0.1% to about 0.5%, about 0.1% to about 0.4%, about 0.1% to about 0.2%, about 0.2% to about 1%, about 0.2% to about 0.8%, about 0.2% to about 0.6%, about 0.2% to about 0.5%, about 0.2% to about 0.4%, about 0.4% to about 1%, about 0.4% to about 0.8%, about 0.4% to about 0.6%, about 0.4% to about 0.5%, about 0.5% to about 1%, about 0.5% to about 0.8%, about 0.5% to about 0.6%, about 0.6% to about 1%, about 0.6% to about 0.8%, or about 0.8% to about 1%) trifluoroacetic acid (TFA) in about 1:10 to about 10:120) isopropanol (IPA): acetonitrile (ACN) (e.g., about 1:50, 1:90, 1:100, 1:120, 10:50, 10:90, or 10:120).

In some embodiments, the reversed phase column is eluted with about 0.01% to about 0.2% (e.g., about 0.01%, about 0.02%, about 0.04%, about 0.05%, about 0.06%, about 0.08%, about 0.1%, about 0.12%, about 0.14%, about 0.15%, about 0.16%, about 0.18%, or about 0.2%) trifluoroacetic acid (TFA) in about 10:90 to about 1:80 isopropanol (IPA): acetonitrile (ACN).

In some embodiments, the reverse phase column is eluted with about 10 mM to about 100 mM (e.g., 10 mM to about 90 mM, about 10 mM to about 80 mM, about 10 mM to about 70 mM, about 10 mM to about 60 mM, about 10 mM to about 50 mM, about 10 mM to about 40 mM, about 10 mM to about 30 mM, about 10 mM to about 20 mM, about 15 mM to about 100 mM, about 15 mM to about 90 mM, about 15 mM to about 80 mM, about 15 mM to about 70 mM, about 15 mM to about 60 mM, about 15 mM to about 50 mM, about 15 mM to about 40 mM, about 15 mM to about 30 mM, about 15 mM to about 20 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 40 mM, about 20 mM to about 30 mM, about 20 mM to about 25 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 40 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 50 mM to about 100 mM, about 50 mM to about 90 mM, about 50 mM to about 80 mM, about 50 mM to about 70 mM, about 50 mM to about 60 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 100 mM, about 80 mM to about 90 mM, or about 90 mM to about 100 mM) sodium acetate, at about pH 2 to about pH 4 (e.g., about pH 2 to about pH 3.8, about pH 2 to about 3.75, about pH 2 to about pH 3.6, about pH 2 to about pH 3.8, about pH 2 to about pH 3.6, about pH 2 to about pH 3.4, about pH 2 to about pH 3.2, about pH 2 to about pH 3.0, about pH 2 to about pH 2.8, about pH 2 to about pH 2.6, about pH 2 to about 2.4, about pH 2 to about pH 2.2, about pH 3 to about pH 4, about pH 3 to about pH 3.8, about pH 3 to about pH 3.75, about pH 3 to about pH 3.6, about pH 3 to about pH 3.4, or about pH 3 to about pH 3.2).

(e) Antibody Reduction

In some embodiments, system 100 includes a sample analyzer that measures reduction of an antibody analyte in a biological sample. In bio-manufacturing production platforms, reductive degradation of antibody products is a concern, and the systems described herein can be used to measure antibody reduction for feedback adjustment of manufacturing process parameters. The antibody reduction can be determined, for example, by a sample analyzer that includes a reversed phase column for performing reversed phase chromatography of the analyte in the sample. Any of the reversed phase column resins, buffers, pH values, and other operating conditions discussed herein can be used in connection with reversed phase chromatography in a sample analyzer.

In some embodiments, hydrophilic interaction chromatography columns can be used to measure product quality attributes for a sample analyte. In certain embodiments, hydrophobic interaction chromatography columns can be used to measure product quality attributes such as oxidation analysis. In some embodiments, lectin columns can be used to obtain product quality attributes that are associated with glycosylation information.

In certain embodiments, enzyme chromatography columns can be used to perform peptide mapping for the purpose of measuring product quality attributes. Reversed phase chromatographic separation can be used to separate peptide analytes for analysis.

The analysis of product quality attributes using system 100 can generally be completed in near-real time, to provide timely control feedback for the adjustment of a wide variety of bio-manufacturing process conditions and parameters. In some embodiments, for example, a concentration or titer attribute for an analyte of a biological sample can be determined, from initial introduction of a portion of the sample on a suitable sample analyzer to a determination of a value of the attribute, in 10 minutes or less (e.g., 9 minutes or less, 8 minutes or less, 7 minutes or less, 6 minutes or less, 5 minutes or less, 4 minutes or less, 3 minutes or less, 2 minutes or less, 1 minute or less).

In certain embodiments, a charge variants or heterogeneity attribute for an analyte of a biological sample can be determined, from initial introduction of a portion of the sample on a suitable sample analyzer to a determination of a value of the attribute, in 70 minutes or less (e.g., 65 minutes or less, 60 minutes or less, 55 minutes or less, 50 minutes or less, 45 minutes or less, 40 minutes or less, 35 minutes or less, 30 minutes or less).

In some embodiments, an aggregation attribute for an analyte of a biological sample can be determined, from initial introduction of a portion of the sample on a suitable sample analyzer to a determination of a value of the attribute, in 30 minutes or less (e.g., 28 minutes or less, 26 minutes or less, 24 minutes or less, 22 minutes or less, 20 minutes or less, 18 minutes or less, 16 minutes or less, 14 minutes or cell, 12 minutes or less, 10 minutes or less).

In certain embodiments, an integrity or purity attribute for an analyte of a biological sample can be determined, from initial introduction of a portion of the sample on a suitable sample analyzer to a determination of a value of the attribute, in 30 minutes or less (e.g., 28 minutes or less, 26 minutes or less, 24 minutes or less, 22 minutes or less, 20 minutes or less, 18 minutes or less, 16 minutes or less, 14 minutes or cell, 12 minutes or less, 10 minutes or less).

For an analysis cycle in which values of each of the four foregoing product quality attributes are determined for an analyte, from initial introduction of a first portion of the biological sample into a first sample analyzer to a determination of the value of the fourth attribute, the elapsed time interval can be 150 minutes or less (e.g., 130 minutes or less, 110 minutes or less, 105 minutes or less, 100 minutes or less, 95 minutes or less, 90 minutes or less, 80 minutes or less, 70 minutes or less, 60 minutes or less).

Figure 3:
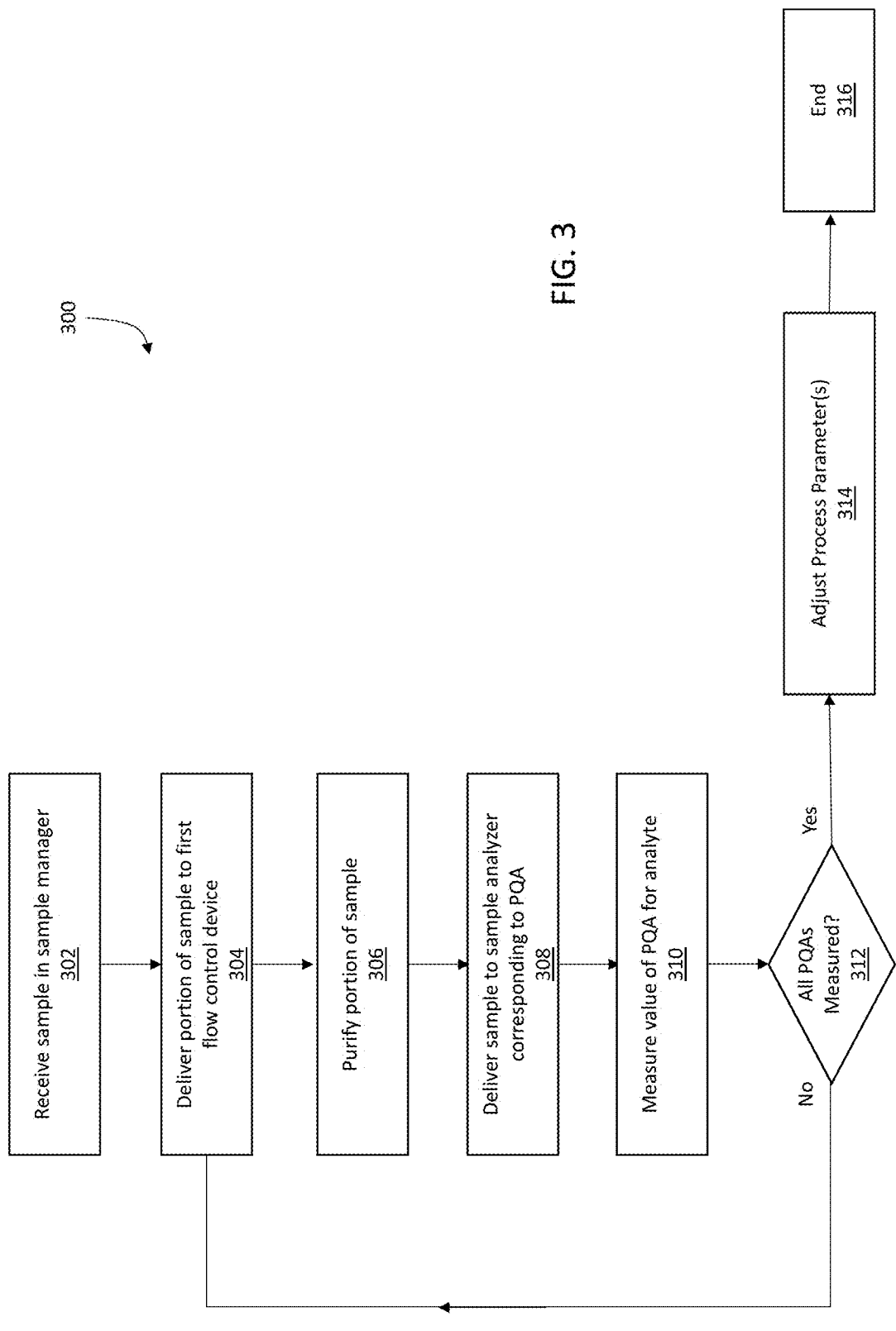
FIG. 3 is a flow chart showing a set of example steps for determining product quality attributes for an analyte of a biological sample.

FIG. 3 is a flow chart 300 that includes a series of example steps for determining product quality attributes for an analyte of a biological sample. In a first step 302, the sample is received in a sample manager. As described above, the sample can be received off-line in a vial, well plate, or other container, from which it is extracted and injected into first flow control device 106. The sample can also be received from an at-line sampling device and held in a fluidic loop or channel, from which portions of the biological sample are injected into first flow control device 106.

Next, in step 304, a portion of the biological sample in injected into the first flow control device 106. The injected portion of the sample can be optionally purified in step 306. Whether purified or not, the portion of the biological sample is delivered to second flow control device 110, from which it is subsequently delivered in step 308 to a sample analyzer associated with a product quality attribute of interest.

Within the sample analyzer, the portion of the biological sample is analyzed to determine a value of the associated product quality attribute for an analyte in the sample in step 310. After the product quality attribute value has been determined, if values of all product quality attributes for the sample analysis cycle have not yet been determined (see step 312), then control returns to step 304 and another portion of the biological sample is injected into the first flow control device 106.

Alternatively, if all product quality attribute values have been determined in step 312, then values of the attributes can optionally be transmitted by control unit 122 to a master controller for adjustment of one or more bio-manufacturing process parameters. The analysis cycle then ends at step 316.

Figure 4A:
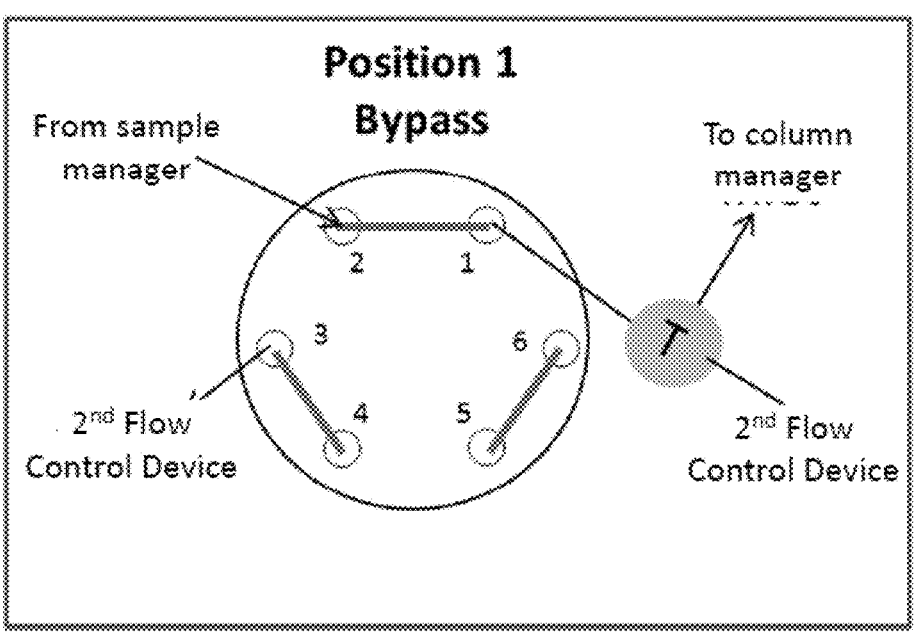
FIGS. 4A-4C are schematic diagrams showing example configurations of flow control devices.
Figure 4B:
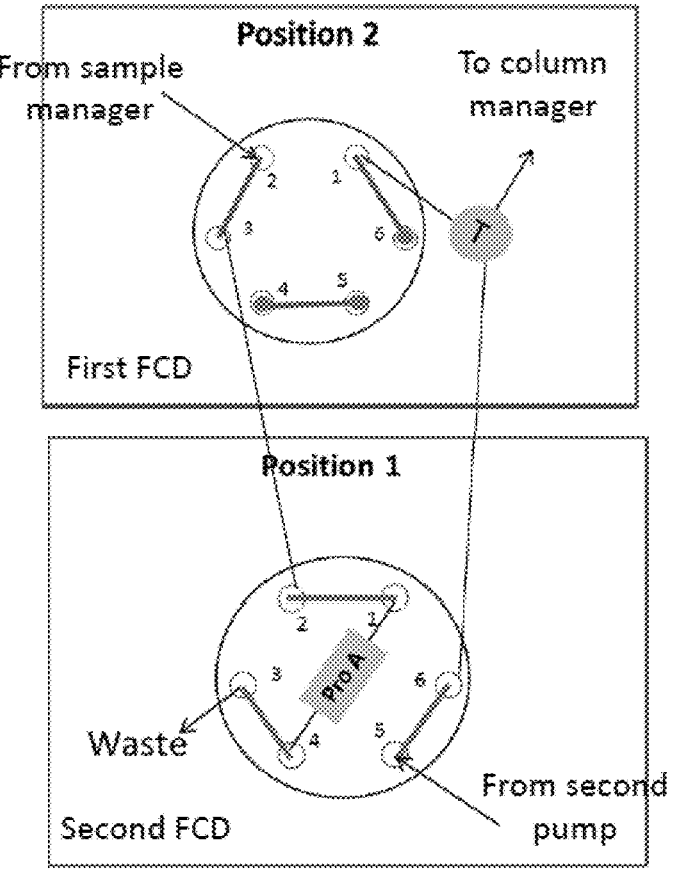
Figure 4C:
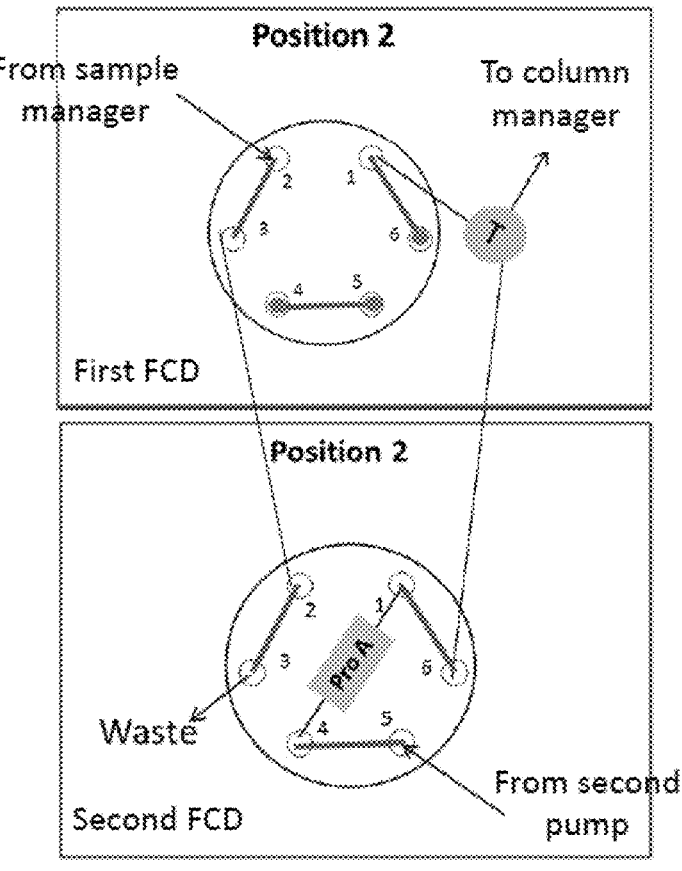

The methods by which a biological sample is delivered from first flow control device 106 either directly to second flow control device 110, or to second flow control device 110 through sample purification device 108, depend on the nature of the flow control devices, among other things. FIGS. 4A-4C show examples of the delivery of the biological sample between first and second flow control devices when the first and second flow control devices are implemented as multi-way valves.

FIG. 4A is a schematic diagram of first flow control device 106 with its configuration adjusted to be in a first position in which ports 1 and 2 are connected, ports 3 and 4 are connected, and ports 5 and 6 are connected. The biological sample is injected into port 2 from sample manager 102. Port 2 is connected to port 1 which in turn is connected to second flow control device 110 and column manager 112. As a result, the sample is directly delivered to second flow control device 110, without passing through sample purification device 108.

FIGS. 4B and 4C are schematic diagrams showing first and second flow control devices 106 and 110 configured to deliver the biological sample to the sample purification device 108. In FIG. 4B, the configuration of the first flow control device is such that the device is in a second position, with ports 2 and 3 connected, ports 4 and 5 connected, and ports 1 and 6 connected. The second flow control device is configured in a first position, with ports 1 and 2 connected, ports 3 and 4 connected, and ports 5 and 6 connected. In addition, sample purification device 108 is connected across ports 1 and 4, port 3 is connected to a waste reservoir, and port 2 is connected to port 3 of the first flow control device. The configuration shown in FIG. 4B is used to load the biological sample onto the column of sample purification device 108, with a loading buffer introduced through port 1 of the first flow control device.

Once the biological sample is loaded onto the sample purification device column, the configurations of first and second flow control devices are adjusted as shown in FIG. 4C to elute the biological sample from the sample purification device column. In this configuration, the second flow control device is adjusted to a different configuration in which ports 2 and 3 are connected, ports 4 and 5 are connected, and ports 1 and 6 are connected. In addition, port 6 of second flow control device 110 is connected to port 1 of first flow control device 106. To elute the analyte from the sample purification device column, an elution buffer is delivered to port 5 of the second flow control device, and the eluted analyte is delivered to the second flow control device, and then into one of the sample analyzers in fluid communication with the second flow control device.

Analyzing biological samples to determine values of product quality attributes according to the systems and methods described herein can be advantageous in various ways. For example, the systems described can function as a single collection platform for many different product quality attributes throughout process development (e.g., cell line development to drug product development), maintaining data continuity and consistency in collection methodology.

In addition, measurements of product quality attributes can be used for spectroscopic model validation and ongoing model validation. Using periodically measured product quality attributes, for example, spectroscopic models can be maintained by validating the prediction accuracy of chemometric methods that use in-line FTIR and/or Raman measurements.

The automated nature of the systems described herein can be used to eliminate tedious, repetitive analytical steps that would otherwise be performed manually, saving time and reducing the likelihood that operator error influences values of the measured attributes. Similarly, integrated sample purification can be performed in-line, significantly reducing the amount of time required to obtain purer biological samples.

The systems and methods described herein can be used to analyze harvested media directly, at a location close to the bioreactor in a manufacturing system. Feedback of information about the measured product quality attributes (e.g., by control unit 122) can, in some embodiments, provide more direct and timely control over manufacturing process parameters that can be adjusted to increase product yields, reduce waste rates, and otherwise improve the efficiency of bio-manufacturing processes.

In addition to applications involving direct assessment of product quality attributes for bio-reactor management, the attribute values can be used in cell line process development. For example, the methods described herein can be applied to determine product quality attributes for a monoclonal antibody therapeutic for the analysis and comparison of different clones.

Integration and Adjustment of Biomanufacturing Systems

The systems disclosed herein can be integrated with bio-manufacturing systems to provide feedback control to various components and steps in synthesis and purification processes for a variety of biological products.

Integrated and fully continuous processes for manufacturing therapeutic protein drugs and other substances can include, e.g., providing a liquid culture medium containing a recombinant therapeutic protein that is substantially free of cells, then feeding the liquid culture medium into a first multi-column chromatography system (MCCS1). The next step involves capturing the recombinant therapeutic protein in the liquid culture medium using the MCCS1, and then continuously feeding the eluate of the MCCS1 containing the recombinant therapeutic protein into a second multi-column chromatography system (MCCS2), and purifying and polishing the protein using the MCCS2. The resulting eluate from the MCCS2 is considered a therapeutic protein drug substance. The processes are integrated and can run continuously from the liquid culture medium to the eluate from the MCCS2 that is the therapeutic protein drug substance.

Bio-manufacturing systems are typically used to perform the above processes. For example, such systems can include a MCCS1 that includes an inlet and a MCCS2 that includes an outlet. In these systems, the first and second MCCSs are in fluid communication with each other. The systems are also configured such that fluid can be passed into the inlet, through the first and second MCCSs, and exit the manufacturing system through the outlet.

Such systems can provide for continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS can be, e.g., between about 4 hours and about 48 hours.

Figure 8:
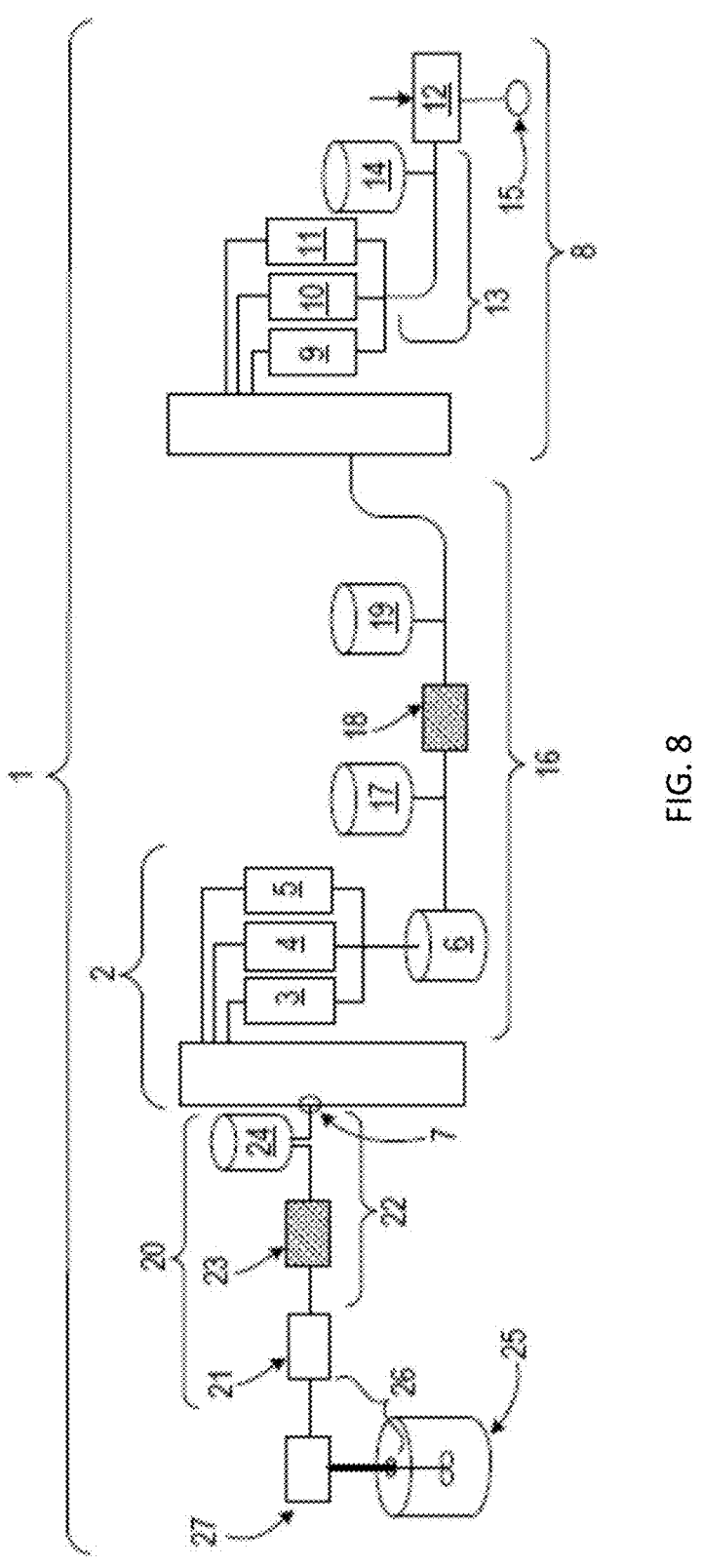
FIG. 8 is a schematic diagram showing an example of a bio-manufacturing system.

FIG. 8 is a schematic diagram showing an example of a bio-manufacturing system. System 1 includes a first MCCS, i.e., a four-column Periodic Counter-Current Chromatography System (PCCS) 2, where three of the four columns 3, 4, and 5 in four-column PCCS 2 perform the unit operation of capturing the recombinant therapeutic protein from a fluid containing the recombinant therapeutic protein (e.g., liquid culture medium that is substantially free of mammalian cells), and one of the columns 6 in PCCS 2 performs the unit operation of inactivating viruses present in the eluate from columns 3, 4, and 5 in PCCS 2 containing the recombinant therapeutic protein. Columns 3, 4, and 5 can contain a resin that utilizes a Protein A-binding capture mechanism. Column 6 is capable of holding a fluid at a pH of about 3.75 for about 1 hour. PCCS 1 also has an inlet 7. Inlet 7 can be, e.g., an orifice that accepts entry of a fluid into PCCS 1.

System 1 also includes a second MCCS that is a PCCS 8 that includes three chromatography columns 9, 10, and 11 and one chromatographic membrane 12. Columns 9, 10, and 11 in PCCS 8 can contain a cationic exchange resin. Chromatographic membrane 12 in PCCS 8 can contain a cationic exchange resin. PCCS 8 also has a fluid conduit 13 disposed between columns 9, 10, and 11 in PCCS 8 and chromatographic membrane 12 in PCCS 8. PCCS 8 also has an in-line buffer adjustment reservoir 14 that is in fluid communication with fluid conduit 13, and is configured such that buffer contained within in-line buffer adjustment reservoir 14 is introduced into the fluid present in fluid conduit 13. PCCS 8 also includes an outlet 15. Outlet 15 can be, e.g., an orifice that allows exit of the fluid from PCCS 8.

System 1 can further include a fluid conduit 16 disposed between PCCS 2 and PCCS 8. System 1 can also include an in-line buffer adjustment reservoir 17 in fluid communication with fluid conduit 16 configured such that the buffer contained within in-line buffer adjustment reservoir 17 can be introduced into the fluid present in fluid conduit 16. System 1 can also include a filter 18 disposed in fluid conduit 16 to filter the fluid present in fluid conduit 16. System 1 can also include a break tank 19 disposed in fluid conduit 16 and configured to hold any fluid in fluid conduit 16 that cannot be readily fed into PCCS 8.

System 1 can further include a pump system 20 that is in fluid communication with inlet 7. Pump system 20 can include a pump 21 for pushing fluid into inlet 7. System 1 can also include a fluid conduit 22 disposed between pump 21 and inlet 7. System 1 can also include a filter 23 disposed in fluid conduit 22 to filter the fluid (e.g., liquid culture medium) present in fluid conduit 22. System 1 can also include a break tank 24 disposed in fluid conduit 22 configured such that break tank 24 is in fluid communication with fluid conduit 22 and is capable of storing any fluid present in fluid conduit 22 that is not able to enter inlet 7.

System 1 can also include a bioreactor 25 and a fluid conduit 26 disposed between bioreactor 25 and pump 21. A filtration system 27 may be disposed in fluid conduit 26 to filter (e.g., remove cells from) a liquid culture medium present in fluid conduit 26.

The first MCCS (PCCS 2) includes an inlet through which fluid (e.g., a liquid culture medium that is substantially free of cells) can be passed into the first MCCS. The inlet can be any structure known in the art for such purposes. It can include, e.g., a threading, ribbing, or a seal that allows for a fluid conduit to be inserted, such that after insertion of the fluid conduit into the inlet, fluid will enter the first MCCS through the inlet without significant seepage of fluid out of the inlet.

The first MCCS includes at least two chromatography columns, at least two chromatographic membranes, or at least one chromatography column and at least one chromatographic membrane, and an inlet. For example, the first MCCS can include a total of four chromatography columns, or three chromatography columns and one chromatographic membrane, or any of the other exemplary MCCSs described herein, or have one or more of any of the exemplary features of a MCCS (in any combination) described herein.

The chromatography column(s) and/or the chromatographic membrane(s) present in the first MCCS can contain one or more of a variety of resins. For example, the resin contained in one or more of the chromatography column(s) and/or chromatographic membrane(s) present in the first MCCS can be a resin that utilizes a capture mechanism (e.g., Protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin contained in one or more of the chromatography column(s) and/or chromatographic membrane(s) of the first MCCS can be a cation exchange resin, an anion exchange resin, a molecular sieve resin, or a hydrophobic interaction resin, or any combination thereof. Additional examples of resins that can be used to purify a recombinant therapeutic protein are known in the art, and can be contained in one or more of the chromatography column(s) and/or chromatographic membrane(s) present in the first MCCS. The chromatography column(s) and/or chromatography membranes present in the first MCCS can contain the same and/or different resins (e.g., any of the resins described herein or known in the art for use in recombinant protein purification).

The two or more chromatography column(s) and/or chromatographic resin(s) present in the first MCCS can perform one or more unit operations (e.g., capturing a recombinant therapeutic protein, purifying a recombinant therapeutic protein, polishing a recombinant therapeutic protein, inactivating viruses, adjusting the ionic concentration and/or pH of a fluid containing the recombinant therapeutic protein, or filtering a fluid containing a recombinant therapeutic protein). In non-limiting examples, the first MCCS can perform the unit operations of capturing a recombinant therapeutic protein from a fluid (e.g., a liquid culture medium) and inactivating viruses present in the fluid containing the recombinant therapeutic protein. The first MCCS can perform any combination of two of more unit operations described herein or known in the art.

The chromatography column(s) and/or chromatographic membrane(s) present in the first MCCS can be connected or moved with respect to each other by a switching mechanism (e.g., a column-switching mechanism). The first MCCS can also include one or more (e.g., two, three, four, or five) pumps (e.g., automated, e.g., automated peristaltic pumps). The column-switching events can be triggered by the detection of a level of recombinant therapeutic protein in the fluid passing through the first MCCS (e.g., the input into and/or eluate from one or more of the chromatography column(s) and/or chromatographic membranes in the first MCCS), a specific volume of liquid (e.g., buffer), or specific time elapsed. Column switching generally means a mechanism by which at least two different chromatography columns and/or chromatographic membranes in an MCCS (e.g., two or more different chromatography columns and/or chromatographic membranes present in an MCCS (e.g., the first or second MCCS)) are allowed to pass through a different step (e.g., equilibration, loading, eluting, or washing) at substantially the same time during at least part of the process.

PCCS 2 that is the first MCCS can include four chromatography columns, where the first three columns perform the unit operation of capturing a recombinant therapeutic protein from a fluid (e.g., a liquid culture medium), and the fourth column of the PCCS performs the unit operation of inactivating viruses in the fluid containing the recombinant therapeutic protein. A PCCS that is the first MCCS can utilize a column-switching mechanism. The PCC system can utilize a modified AKTA system (GE Healthcare, Piscataway, NJ) capable of running up to, e.g., four, five, six, seven, or eight columns, or more.

Column switching events can be triggered by detection of a concentration of a particular protein or other substance in a fluid eluting from one of the columns of PCCS 2 or PCCS 8, flowing through a filter in the MCCS, contained in a break tank of the MCCS, or flowing through a conduit in the MCCS (e.g., between MCCS 1 and MCCS 2). The measurement systems disclosed herein can be used to measure concentrations of such proteins, and to transmit the concentration information to a controller in system 1 that initiates events such as column switching, filtering, and fluid transport in system 1.

The first MCCS can be equipped with: one or more (e.g., two, three, four, five, six, seven, eight, nine, or ten) measurement systems configured to obtain infrared spectroscopic information for process fluids (e.g., system 100), one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The first MCCS can also be equipped with a controller executing an operating system that utilizes software (e.g., Unicorn-based software, GE Healthcare, Piscataway, NJ, or other software implementing similar functionality) for determining when a column-switching should occur (e.g., based upon concentration information derived from infrared spectroscopic measurements, volume of liquid, or elapsed time) and affecting (triggering) the column-switching events. The measurement systems can be placed optionally at the inlet of one or more (e.g., two, three, four, five, six, seven, eight, nine, or ten) of the chromatography column(s) and/or chromatographic membrane(s) in the first MCCS, and/or at the outlet of one or more of the chromatography column(s) and/or chromatography membrane(s) in the first MCCS.

The first MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the first MCCS can include one or more (e.g., two, three, four, five, or six) break tanks that can hold fluid that cannot readily pass into one or more of the chromatography columns and/or chromatographic membranes in the first MCCS. The systems described herein can contain one or more break tanks (e.g., a break tank described herein) in the first and/or second MCCS. Other examples of the systems described herein do not include a break tank in the first MCCS or the second MCCS, or do not include a break tank in the entire system. Other examples of the systems include a maximum of one, two, three, four, or five break tank(s) in the entire system.

In some embodiments, the first MCCS can include a viral inactivation device. For example, referring to FIG. 8, in certain embodiments the first MCCS includes viral inactivation device 6 (i.e., in place of column 6 described above). Viral inactivation device 6 is configured to inactivate viruses and viral vectors used in bio-manufacturing processes. In some embodiments, for example, viral inactivation device 6 includes a mixing vessel. Alternatively, in certain embodiments for example, device 6 includes a plug flow inactivation system. Each of these examples of viral inactivation devices helps to eliminate active viruses and viral vectors from process fluids in the first MCCS.

The second MCCS includes at least two chromatography columns, at least two chromatographic membranes, or at least one chromatography column(s) and at least one chromatographic membrane(s), and an outlet. For example, the second MCCS can include a total of four chromatography columns, three chromatography columns and one chromatographic membrane, or any of the other exemplary MCCSs described herein, or can have one or more of any of the exemplary features of an MCCS (in any combination) described herein. The chromatography column(s) and/or the chromatographic membrane(s) present in the second MCCS can have one or more of: any of the shapes, sizes, volumes (bed volumes), and/or unit operations described herein. The resin contained in one or more of the chromatography column(s) and/or chromatographic membrane(s) present in the second MCCS can be a resin that utilizes a capture mechanism (e.g., Protein A-binding capture mechanism, Protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). Useful resins include, e.g., a cation exchange resin, an anion exchange resin, a molecular sieve resin, and a hydrophobic interaction resin. The chromatography column(s) and/or chromatography membranes present in the second MCCS can contain the same and/or different resins (e.g., any of the resins described herein or known in the art for use in recombinant protein purification).

The chromatography column(s) and/or chromatographic membrane(s) present in the second MCCS can perform one or more unit operations (e.g., any of the unit operations described herein or any combination of the unit operations described herein). In non-limiting examples, the second MCCS can perform the unit operations of purifying a recombinant therapeutic protein from a fluid and polishing the recombinant therapeutic protein present in the fluid containing the recombinant therapeutic protein. In other non-limiting examples, the second MCCS can perform the unit operations of purifying a recombinant therapeutic protein present in a fluid, polishing a recombinant therapeutic protein present in a fluid, and filtering a fluid containing a recombinant therapeutic protein. In another example, the second MCCS can perform the unit operations of purifying a recombinant therapeutic protein present in a fluid, polishing a recombinant therapeutic protein present in a fluid, filtering a fluid containing a recombinant therapeutic protein, and adjusting the ionic concentration and/or pH of a fluid containing a recombinant therapeutic protein. The second MCCS can perform any combination of two of more unit operations described herein or known in the art.

The second MCCS can also include one or more (e.g., two, three, four, or five) pumps (e.g., automated, e.g., automated peristaltic pumps).

The chromatography column(s) and/or chromatographic membrane(s) present in the second MCCS can be connected or moved with respect to each other by a switching mechanism (e.g., a column-switching mechanism). The column-switching events can be triggered by the detection of a level of recombinant therapeutic protein or other substance via infrared spectroscopic measurements and analysis thereof using chemometric models, as discussed above, to determine the level of recombinant therapeutic protein in the fluid passing through the second MCCS (e.g., the input into and/or eluate from one or more of the chromatography column(s) and/or chromatographic membranes in the second MCCS), a specific volume of liquid (e.g., buffer), or specific time elapsed.

The PCCS 8 that forms the second MCCS can contain three columns that perform the unit operation of purifying a recombinant therapeutic protein from a fluid, and a chromatographic membrane that performs the unit operation of polishing a recombinant therapeutic protein present in a fluid. For example, the three columns that perform the unit operation of purifying a recombinant therapeutic protein from a fluid can contain, e.g., a cationic exchange resin, and the chromatographic membrane that performs the unit operation of polishing can contain a cationic exchange resin. A PCCS that is the second MCCS can utilize a column-switching mechanism. For example, the PCCS can utilize a modified AKTA system (GE Healthcare, Piscataway, NJ) capable of running up to, e.g., four, five, six, seven, or eight columns, or more.

Similar to the first MCCS, the second MCCS can also be equipped with: one or more (e.g., two, three, four, five, six, seven, eight, nine, or ten) infrared spectroscopic measurement systems, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The one or more measurement systems transmit concentration information for the protein or other substance in the fluid that is measured to a controller that uses the concentration information to determine whether to trigger a column switching event. The second MCCS can be equipped with an operating system, executed by the controller that receives the concentration information, that utilizes software (e.g., Unicorn-based software, GE Healthcare, Piscataway, NJ) for determining when a column-switching event should occur (e.g., based upon infrared spectroscopic measurements, volume of liquid, or elapsed time) and initiating the column-switching events. In the examples where the second MCCS includes one or more infrared spectroscopic measurement systems, the measurement systems can be placed optionally at the inlet of one or more (e.g., two, three, four, five, six, seven, eight, nine, or ten) of the chromatography column(s) and/or chromatographic membrane(s) in the second MCCS, and/or at the outlet of one or more of the chromatography column(s) and/or chromatography membrane(s) in the second MCCS.

The second MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the second MCCS can include one or more (e.g., two, three, four, five, or six) break tanks (e.g., any of the break tanks described herein) that can hold fluid that cannot readily pass into one or more of the chromatography columns and/or chromatographic membranes in the second MCCS.

The second MCCS includes an outlet through which the therapeutic protein drug substance can exit the system. The outlet can include, e.g., a threading, ribbing, or a seal that allows for a fluid conduit to be inserted or a vial designed to contain or store the therapeutic protein drug substance. An outlet can contain a surface that can be used to seal a sterile vial or other such storage container onto the outlet in order to allow the recombinant protein drug product to flow directly into the sterile vial or storage container.

Any of the fluid conduits described herein can be, e.g., a tube that is made of, e.g., polyethylene, polycarbonate, or plastic. The fluid conduit disposed between the first MCCS and the second MCCS can further include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; a break tank (e.g., any of the break tank(s) described herein) that is in fluid communication with the fluid conduit and is positioned such that it can hold any excess fluid present in the fluid conduit that is unable to readily feed into the second MCCS; and one or more filters that are disposed in the fluid conduit such that they are capable of filtering (e.g., removing bacteria) the fluid present in the fluid conduit. Any of the in-line buffer adjustment reservoirs can contain, e.g., a volume of between about 0.5 L to 50 L of buffer (e.g., at a temperature at or below 50° C., 37° C., 25° C., 15° C., or 10° C.).

The systems described herein can optionally include a fluid conduit disposed between the final chromatography column or chromatographic membrane in the second MCCS and the outlet. The systems described herein can further include one or more filters in fluid connection with the fluid conduit disposed between the final chromatography column or chromatographic membrane in the second MCCS and the outlet, such that the filter can remove, e.g., precipitated material, particulate matter, or bacteria from the fluid present in the fluid conduit disposed between the final chromatography column or chromatographic membrane in the second MCCS and the outlet.

Some examples of the systems provided herein also include a bioreactor that is in fluid connectivity with the inlet of the first MCCS. Any of the exemplary bioreactors described herein or known in the art can be used in the present systems.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks (e.g., any of the break tanks described herein). Some examples of the systems provided herein further include a fluid conduit disposed between the pump and the inlet of the first MCCS (e.g., any of the exemplary fluid conduits described herein or known in the art). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

Some examples of the systems described herein further include a further fluid conduit connected to the fluid conduit between the pump and the inlet, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system).

The foregoing bio-manufacturing systems allow for the continuous production of a therapeutic protein drug substance. For example, the systems provided herein allow for a percentage yield of recombinant therapeutic protein (from a starting material, e.g., a starting liquid culture medium) of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The systems described herein can also result in a percentage yield of recombinant therapeutic protein (from a starting material, e.g., a starting liquid culture medium) of between about 80% to about 90%, between about 82% to about 90%, between about 84% to about 90%, between about 84% to about 88%, between about 84% to about 94%, between about 82% to about 92%, or between about 85% to about 95%.

The systems described herein can also result in the production of a therapeutic protein drug substance that contains a concentration of recombinant therapeutic protein that is greater than about 1.0 mg/mL, e.g., greater than about 15 mg/mL, greater than about 20 mg/mL, greater than about 25 mg/mL, greater than about 30 mg/mL, greater than about 35 mg/mL, greater than about 40 mg/mL, greater than about 45 mg/mL, greater than about 50 mg/mL, greater than about 55 mg/mL, greater than about 60 mg/mL, greater than about 65 mg/mL, greater than about 70 mg/mL, greater than about 75 mg/mL, greater than about 80 mg/mL, greater than about 85 mg/mL, greater than about 90 mg/mL, greater than about 100 mg/mL, greater than about 125 mg/mL, or greater than about 150 mg/mL.

As discussed above, in some embodiments, the first and/or second MCCS can be a Periodic Counter-Current Chromatography System (PCCS). A PCCS can, e.g., include two or more chromatography columns (e.g., three columns or four columns) that are switched in order to allow for the continuous elution of recombinant therapeutic protein from the two or more chromatography columns. A PCCS can include two or more chromatography columns, two or more chromatographic membranes, or at least one chromatographic column and at least one chromatographic membrane. A column operation generally consists of the load, wash, elute, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography.

Figure 9:
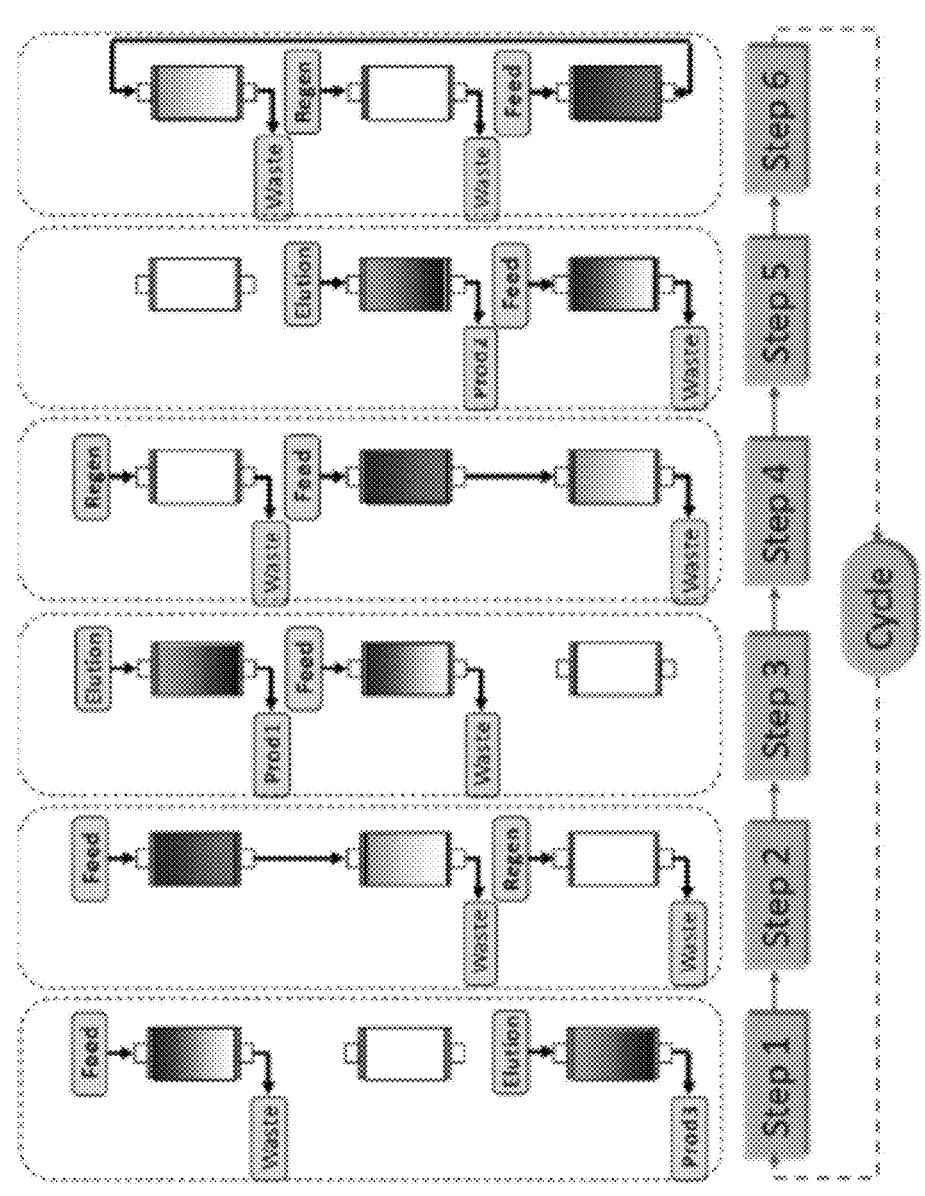
FIG. 9 is a schematic diagram showing an example of a three column-switching technique.

An example of the three column-switching technique used in a PCCS containing three columns is shown in FIG. 9. A cycle is defined as three complete column operations resulting in an elution pool from each of the three columns used in the column-switching technique. Once all the steps in the cycle are completed, the cycle is re-started. As a result of the continuous cycling and elution, fluid entering a PCCS is processed continuously, while recombinant therapeutic protein elution from each column is discrete and periodic.

To advance from one step to another in a PCCS cycle, such as the exemplary cycle shown in FIG. 9, a column-switching strategy is employed. The column switching method employs two automated switching operations per column in the three-columns in the exemplary PCCS system shown in FIG. 9, the first of which is related to the initial product breakthrough, while the second coincides with column saturation. The determination of when the column switching operations should take place is based on information about recombinant therapeutic protein concentrations in the eluate from each chromatography column in the PCCS.

As discussed above, a suitable sample analyzer can be used to determine concentrations of recombinant therapeutic proteins in eluate from PCCS columns. The concentration information—which functions as a feedback control for the bio-manufacturing system—is transmitted to the MCCS controller by control unit 122, which initiates column switching after determining that a switch is warranted.

As an example, during column loading, the PCC control system can determine a baseline concentration of a therapeutic protein substance eluting from the column (which is typically zero concentration) using the infrared spectroscopic measurement systems discussed above. During active elution, as the protein substance breaks through, there is an increase (e.g., above the baseline concentration) in the measured protein concentration. The system continues to monitor the increasing protein concentration, and when the concentration reaches a pre-determined threshold value, the flow-through from column 1 is directed onto column 2 instead of to the waste. Nominally, this occurs at a time $t_1$.

As the feed continues into column 1, column 1 eventually becomes nearly saturated with the protein product. At this point, the measured concentration of protein in the eluate has reached another pre-determined value, which occurs at a time t2. At this point, the MCCS controller switches the inlet feed to column 2.

The above column-switching strategy allows for the uniform loading of the columns irrespective of the feed product concentration and the capacity. Similar switches of the columns based on the level of recombinant protein detected in the eluate from each column can be implemented. Column switches can also be based on elapsed time or the amount of fluid (e.g., buffer) passed through the one or more chromatography column(s) and/or chromatographic membranes in the first or second MCCS.

In addition to providing feedback information to control column switching events, the measurement systems disclosed herein can also provide feedback information for the adjustment of various other bio-manufacturing steps and operating parameters. One example of such adjustments is the controlled adjustment of buffer concentrations at various stages of the bio-manufacturing processes.

In general, one or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the two or more MCCSs in any of the processes described herein. As is known in the art, the one or more types of buffer used in the two or more MCCSs used in the processes described herein will depend on the resin present in the chromatography column(s) and/or the chromatographic membrane(s) of the two or more MCCSs (e.g., the first and second MCCSs), the recombinant therapeutic protein, and unit operation (e.g., any of the exemplary unit operations described herein) performed by the specific chromatography column(s) and/or chromatography membranes of the two or more MCCSs. The volume and type of buffer employed during the use of the two or more MCCSs in any of the processes described herein can also be determined by one skilled in the art (e.g., discussed in more detail below). For example, the volume and type(s) of buffer employed during the use of the two or more MCCSs in any of the processes described herein can be chosen in order to optimize one or more of the following in the recombinant protein drug product: the overall yield of recombinant therapeutic protein, the activity of the recombinant therapeutic protein, the level of purity of the recombinant therapeutic protein, and the removal of biological contaminants from a fluid containing the recombinant therapeutic protein (e.g., absence of active viruses, mycobacteria, yeast, bacteria, or mammalian cells).

The unit operations of adjusting the ionic concentration and/or pH of a fluid containing the recombinant therapeutic protein can be performed using a MCCS (e.g., the first and/or second MCCS) that includes and utilizes a buffer adjustment reservoir (e.g., an in-line buffer adjustment reservoir) that adds a new or additional buffer solution into a fluid that contains the recombinant therapeutic protein (e.g., between columns within a single MCCS, or after the last column in a penultimate MCCS (e.g., the first MCCS) and before the fluid containing the recombinant therapeutic protein is fed into the first column of the next MCCS (e.g., the second MCCS). The in-line buffer adjustment reservoir can be any size (e.g., greater than 100 mL) and can contain any buffered solution (e.g., a buffered solution that has one or more of: an increased or decreased pH as compared to the fluid containing the recombinant therapeutic protein, an increased or decreased ionic (e.g., salt) concentration compared to the fluid containing the recombinant therapeutic protein, and/or an increased or decreased concentration of an agent that competes with the recombinant therapeutic protein for binding to resin present in at least one chromatographic column or at least one chromatographic membrane in an MCCS (e.g., the first or the second MCCS)).

In some embodiments, determination by the MCCS controller of the amount of buffer solution to add to process fluid is based on concentration or titer information for an analyte in a biological sample. For example, the solute for purposes of such measurements can be a buffer solution component or a component of the process fluid for which the concentration is related to the fluid buffer composition, the pH of the process fluid, and/or the ionic strength of the process fluid. Measurement of the concentration information for the component is provided as feedback information to the MCCS controller, which uses the feedback information to determine when and what quantity of one or more buffer solutions to discharge into the process fluid. Infrared spectroscopic measurement systems can generally be positioned at any location in the bio-manufacturing system for purposes of measuring process fluids to provide buffer-related feedback information to the MCCS controller.

In certain embodiments, antibody concentration information for a process fluid can be used to control a rate at which cell cultures are introduced into a bioreactor. In particular, by determining the antibody concentration value in a process fluid harvested from the bioreactor, the MCCS controller can adjust the bleed rate of the cell culture into the bioreactor. Adjustment in this manner allows control of the volumetric productivity derived from cell density and specific productivity of the bioreactor. For a fixed perfusion rate, such adjustments permit control of the antibody concentration in the process fluid such that MCCS1 would receive an approximately constant amount of product per unit time. In other words, adjustments of this nature can be used to ensure that the rate of product generation within the bioreactor remains approximately constant over a particular time period.

In some embodiments, determination of certain quality attributes associated with process fluids can be used by the MCCS controller to determine whether a bio-manufacturing system is operating within an acceptable range of parameters, or whether during operation, the system is outside one or more acceptable parameter ranges.

For each of one or more quality attributes, a range of acceptable values can be established through calibration procedures. These ranges effectively establish operating conditions for the system under which biological products are generated at acceptable rates and levels of purity, while the yields of by-products and other undesirable species are at acceptably low levels. When the system operates outside of one or more of the ranges, product yields and/or purity may be reduced, rates/quantities of production of undesirable species may be increased, reagent consumption rates may be increased, and/or other undesirable effects or conditions may result.

Quality attributes determined for process fluids at one or more locations within the system can be used to ensure that the system operates within acceptable ranges of these operating parameters. If the determined values of one or more of the quality attributes fall outside the established acceptable ranges, the MCCS controller identifies that a potential fault condition exists.

To address a fault condition, the MCCS controller (or another system controller connected to the MCCS controller) can adjust any of the operating parameters of the bio-manufacturing system to modify its operation, thereby also adjusting values of the quality attributes such that they fall within acceptable ranges. Corrective actions of this nature ensure that, based on feedback provided by the determined values of the quality attributes, the system can be actively maintained within an established set or range of operating conditions.

In certain embodiments, if the MCCS controller (or another system controller connected to the MCCS controller) determines that the system is too far out of range from its acceptable range of operating conditions such that returning the system to an acceptable range of conditions would be difficult or even impossible, or would result in other undesirable consequences, the controller can transmit control signals to the bioreactor to discontinue production and discharge its contents to waste. In such a case, effective corrective action is impractical or impossible—the production process has deviated too far from the acceptable range of operating conditions for the system. By simply discharging the contents of the bioreactor, the system can save considerable time by restarting the production process, rather than attempting to adjust an ongoing production process that may have deviated irretrievably from an acceptable range of conditions.

Further, feedback can be provided to the MCCS controller (or to another system controller) based on measured values of one or more bioreactor medium components (such as glucose concentration, glutamine concentration, lactate concentration, and ammonium ion concentration), which can then be used to adjust reactor conditions to ensure that cell viability, product yields, and other performance metrics are maintained within target ranges. Any one or more process parameters can be adjusted by the controller based on values of the bioreactor medium components in a manner similar to adjustments made based on product quality attributes and values of other measured quantities.

Hardware and Software Implementation

Control unit 122 can be configured to perform any of the control functions described herein, and can be implemented in hardware, in software, or in a combination of both hardware and software. Control unit 122 typically includes at least one electronic processor connected to a memory unit, a storage device, an output device (e.g., a display), and a human interface device (e.g., a keyboard, mouse, touchpad, touch-sensitive display). Control unit 122 receives information as electrical signals from system components along some or all of the control lines shown herein, and transmits electrical control signals along the control lines to the system components.

The method steps and control functions described herein can be implemented in computer programs using standard or proprietary programming languages. Such programs are designed to be executed by control unit 122 (e.g., the electronic processor of the control unit), and cause the control unit to perform the steps and functions described. Each program can be stored on a computer readable storage medium (e.g., an optical, magnetic, solid-state, re-writable, or other persistent storage medium). An example of a propriety programming language that can be used to provide instructions to control unit 122 is the Empower® software suite (Waters Corp., Milford, MA).

EXAMPLES

The following examples are provided to further illustrate various aspects of the foregoing disclosure, but are not intended to otherwise limit any features of the claims, or limit any aspects of the embodiments unless expressly stated.

Example 1

System 100 was used to analyze anti-TGFβ from a perfusion bioreactor being run with an intensified perfusion process. The system included a Process Sample Manager (PSM), Column Heater (CH), Column Manager (CM) containing two 1-position, 9-port valves, Binary Pump (BSM), Quaternary Pump (QSM) with added solvent select valve on the "D" line, a PDA detector (PDA), a 2-position, 10-port column select valve housing a 5 mL stainless steel sample holding loop (all obtained from Waters Corp., Milford, MA), and two IDEX auxiliary 2-position, 6-port switching valves.

Harvest from the bioreactor was automatically sampled using the MAST (modular automated sampling technology) (obtained from Lonza, Basel, Switzerland) connected to a liquid handler (obtained from Gilson, Middleton, WI). The MAST system pulled ~40 mL of harvest by positive displacement pumps to clear the lines before depositing 10 mL of harvest into a clear 12 mL glass vial on the liquid handler deck. The liquid handler then transferred 7.5 mL of harvest to system 100 through the reinjection of the material into a PEEK tubing transfer line connecting both the liquid handler and the suction. The sample was transferred directly to the 5 mL sample holding loop where it was held until sample analysis.

Once sample transfer had been completed, the MAST computer sent a signal to control unit 122 to initialize the method set specified in Empower® 3 software.

The method set run for this example included a loop load function, two injections on a Protein A (Pro A) column of a sample purification device at two mass loads, two injections on a size exclusion column at 2 mass loads, intermediate water wash methods between separation techniques (Pro A and size exclusion chromatography (SEC)) of the common system components and finally a loop clean with 20% methanol and finish segment to ensure the loop was in the correct position to accept more sample. It should be noted that whenever a secondary column is mentioned (such as SEC), it should be assumed that this method contains inline purification by Pro A unless otherwise stated.

For each injection, 1 mL of harvest was pulled from the holding loop and transferred to a 50 μL sample injection loop for a full loop injection on the system. To test varying mass loads, both a full loop injection was performed as well as an online 1:2 dilution using a 1× phosphate buffered saline (PBS) pH 7.2 buffer.

Sample purification for titer analysis was performed on a Thermo POROS A 2.1×30 mm, 20 μm column (i.e., a Protein A affinity column). The gradient details for the first and second pumps are shown in Tables 1 and 2.

TABLE 1

| First (Binary) Pump Method Parameters for Titer Analysis | | | |
| --- | --- | --- | --- |
| Time (min) | Flow Rate (mL/min) | Buffer A (%) | Buffer B (%) |
| 0.00 | 0.250 | 100 | 0 |
| 1.00 | 0.250 | 100 | 0 |
| 1.10 | 1.000 | 100 | 0 |
| 2.10 | 1.000 | 100 | 0 |
| 2.20 | 0.100 | 100 | 0 |
| 2.40 | 0.100 | 100 | 0 |
| 2.50 | 0.500 | 100 | 0 |
| 2.90 | 0.500 | 100 | 0 |
| 3.00 | 0.100 | 100 | 0 |
| 3.20 | 0.100 | 100 | 0 |
| 3.30 | 0.750 | 0 | 100 |
| 4.80 | 0.750 | 0 | 100 |
| 5.00 | 1.000 | 100 | 0 |
| 7.00 | 1.000 | 100 | 0 |
| 7.50 | 0.000 | 100 | 0 |

TABLE 2

| Second (Quaternary) Pump Method Parameters for Titer Analysis | | |
| --- | --- | --- |
| Time (min) | Flow Rate (mL/min) | Buffer A (%) |
| 0.00 | 0.750 | 100 |
| 2.10 | 0.750 | 100 |
| 2.20 | 0.100 | 100 |
| 2.40 | 0.100 | 100 |
| 2.50 | 1.200 | 100 |
| 2.90 | 1.200 | 100 |
| 3.00 | 0.100 | 100 |

TABLE 2-continued

| Second (Quaternary) Pump Method Parameters for Titer Analysis | | |
| --- | --- | --- |
| Time (min) | Flow Rate (mL/min) | Buffer A (%) |
| 3.20 | 0.100 | 100 |
| 3.30 | 0.750 | 100 |
| 7.00 | 0.750 | 100 |
| 7.50 | 0.000 | 100 |

For the method shown in Table 1, Buffer A was 1× Dulbecco's Phosphate Buffered Saline at pH 7.2, and Buffer B was 20 mM sodium phosphate, 1 M sodium chloride, and 7.5% Isopropanol at pH 8.0. For the method shown in Table 2, Buffer A was 0.1 M phosphate-citrate, 0.14 M sodium chloride at pH 3.2.

The system was configured to direct the purified sample directly to detector 116 (a PDA detector) without passing through any column-based sample analyzers. Separation was monitored at an absorbance of 280 nm. The Protein A column was kept at room temperature in an ambient environment. Upon detection in the PDA detector, the measured chromatogram was integrated to calculate the area under the curve for the peak corresponding to eluted protein at ~2.5 min. The area of the monoclonal antibody was then quantitated through use of a calibration curve built from 50 μg to 2 μg mass loads on column plotted against area.

Figures 5A, 5B:
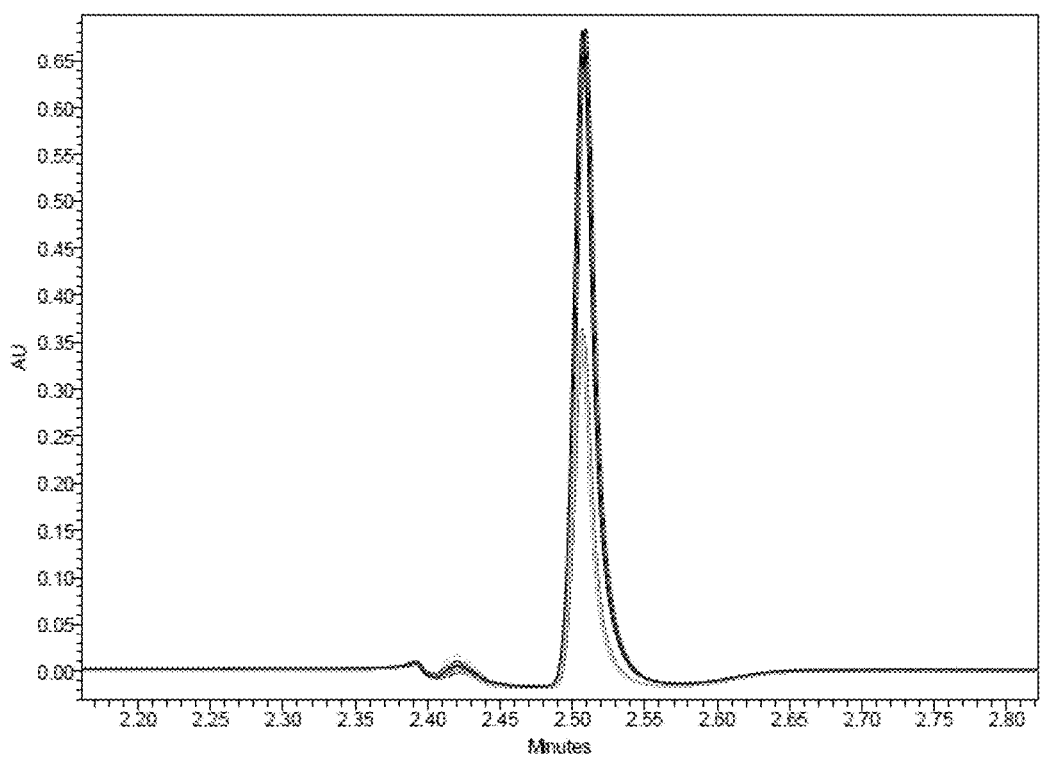
FIG. 5A is a graph showing titer chromatograms for multiple samples.
FIG. 5B is table showing calculated mass loads and concentrations for multiple samples.

FIG. 5A is a graph showing titer chromatograms for a neat sample and a 1:2 diluted sample, and FIG. 5B is table showing calculated mass loads and concentrations from 6 different runs at each dilution ratio. The data show excellent reproducibility between runs, both visually and among the calculated results.

Aggregation analysis was performed using a size exclusion separation method on a Waters UPLC BEH SEC 4.6×300 mm, 1.7 μm, and 200 Å column. The gradient details for the first and second pumps are shown in Tables 3 and 4.

TABLE 3

| First (Binary) Pump Method Parameters for Aggregation Analysis | | | |
| --- | --- | --- | --- |
| Time (min) | Flow Rate (mL/min) | Buffer A (%) | Buffer B (%) |
| 0.00 | 0.250 | 100 | 0 |
| 1.00 | 0.250 | 100 | 0 |
| 1.10 | 1.000 | 100 | 0 |
| 2.10 | 1.000 | 100 | 0 |
| 2.20 | 0.000 | 100 | 0 |
| 2.40 | 0.000 | 100 | 0 |
| 2.50 | 0.500 | 100 | 0 |
| 8.00 | 0.500 | 100 | 0 |
| 8.10 | 0.000 | 100 | 0 |
| 8.30 | 0.000 | 100 | 0 |
| 8.40 | 0.750 | 0 | 100 |
| 10.00 | 0.750 | 0 | 100 |
| 10.20 | 1.000 | 100 | 0 |
| 13.50 | 1.000 | 100 | 0 |
| 14.00 | 0.000 | 100 | 0 |
| 22.50 | 0.000 | 100 | 0 |

TABLE 4

| | Second (Quaternary) Pump Method Parameters for Aggregation Analysis | | |
|---|---|---|---|
| Time (min) | Flow (mL/min) | Buffer A (%) | Buffer B (%) |
| 0.00 | 0.500 | 100 | 0 |
| 2.10 | 0.500 | 100 | 0 |
| 2.20 | 0.000 | 100 | 0 |
| 2.40 | 0.000 | 100 | 0 |
| 2.50 | 0.100 | 100 | 0 |
| 5.00 | 0.100 | 100 | 0 |
| 5.50 | 0.100 | 0 | 100 |
| 8.00 | 0.100 | 0 | 100 |
| 8.10 | 0.000 | 0 | 100 |
| 8.30 | 0.000 | 0 | 100 |
| 8.40 | 0.350 | 0 | 100 |
| 22.00 | 0.350 | 0 | 100 |
| 22.50 | 0.000 | 0 | 100 |

For the method shown in Table 3, Buffer A was 1× Dulbecco's Phosphate Buffered Saline pH 7.2, and Buffer B was 20 mM sodium phosphate, 1 M sodium chloride, and 7.5% Isopropanol at pH 8.0. For the method shown in Table 4, Buffer A was 0.1 M phosphate-citrate and 0.14 M sodium chloride at pH 3.2, and Buffer B was 1× Dulbecco's Phosphate Buffered Saline at pH 7.2.

The column manager was configured to direct the sample to the sample analyzer with the size exclusion chromatography column. Separation of the analyte and other components was monitored at an absorbance of 280 nm. The size exclusion column was kept at 25° C. in a 30 cm column heater while the Protein A column was in an ambient environment. Upon detection in the PDA detector 116, the recorded chromatogram was integrated to calculate the area under the curve for the peaks corresponding to high molecular weight species (before the main peak), main species and low molecular weight species (after the main peak).

Figure 6A:
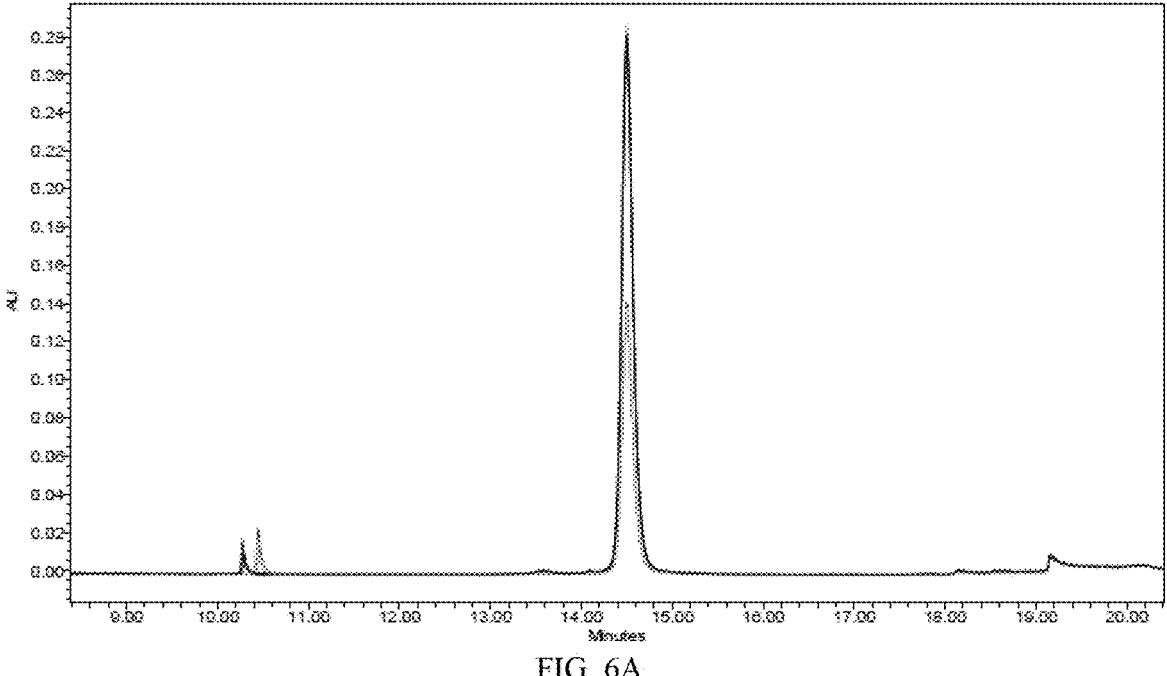
FIG. 6A is a graph showing titer chromatograms for multiple samples.
Figures 6B, 7:
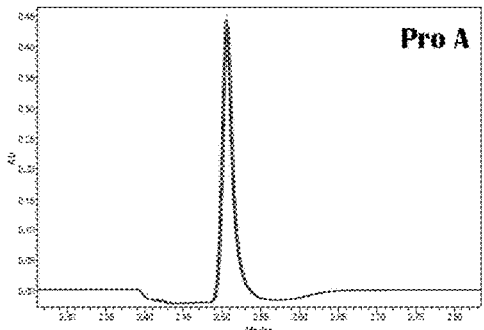
FIG. 6B is a set of tables with measured peak information for different samples.
FIG. 7 is a graph showing measured chromatograms for a set of samples.

FIG. 6A is a graph showing titer chromatograms for a neat sample and a 1:2 diluted sample, and FIG. 6B shows tables with measured peak information for 6 different samples at each of two dilutions. The data show excellent reproducibility between runs, both visually and among the calculated results. Some differences exist in peak percentages between the mass loads which could be a consequence of the column itself.

FIG. 7 is a graph showing measured chromatograms from an experiment in which samples were obtained every 1.5 hours, for a total of 12 samples. For these experiments, only 1 mass load was delivered to both Protein A and size exclusion chromatography columns: a 1:2 online dilution on the sample manager with 1×PBS at pH 7.2. Both titer and aggregation product quality attribute showed excellent reproducibility among the 12 samples.

For reversed phase analysis, separation was performed on a Waters BioResolve Polyphenyl 2.1×100 mm, 2.7 μm, 450 Å column using 0.1% trifluoroacetic acid in water (mobile phase A), 0.1% trifluoroacetic acid in 10% isopropanol, 90% acetonitrile (mobile phase B) and 20 mM sodium acetate pH 3.75 (Protein A column eluent). For strong cation exchange analysis, separation was performed on a Thermo MAbPac SCX-10 RS, 2.1×150 mm, 5 μm column. The mobile phases were 20 mM sodium acetate pH 3.75 (both mobile phase A and Protein A eluent) and 20 mM tris acetate, 25 mM sodium chloride pH 9.8 (mobile phase B). Currently this method employs the use of gradient curvature to create an "S" shaped gradient for optimal peak resolution.

The foregoing methods were used to analyze at-line samples. As discussed above, system 100 can also analyze off-line samples using, for example, a sample manager flow-through needle module (available from Waters Corp., Milford, MA). Using a flow-through needle, a sample is injected directly from a vial or well plate. The injection volume can be varied as desired from 1 μL to 100 μL. This flexibility allows for varying mass loads on columns without performing an online dilution. Additionally, there is no sample holding loop in this system version as all sample volume is contained within the vial or well plate and multiple injections are allowed for each vial.

Example 2. Application of MIMICS-mPQA to at-Line Process Monitoring of Process Development and Pilot Scale Bioreactors Experimental Overview The MIMICS-mPQA platform was applied to the at-scale 100 L run of anti-TGFβ monoclonal therapeutic antibody. Harvest samples were run on the MIMICS-mPQA platform to gather at-line product quality information for 3 attributes: titer, aggregation and purity/integrity.

The samples analyzed were harvest material (post-ATF) from the 100 L bioreactor and 2 satellite 3 L bioreactors. For the analysis, a Protein A (Pro A) affinity column was used for titer determination, a Protein A column in-line with a size exclusion (SEC) column for aggregation analysis and a Protein A column in-line with a reversed phase (RP) column for purity/integrity information. The testing occurred over the course of a 4-week period in which samples were run in blocks of ~4 harvest days from all reactors within each queue. During the analysis time, system mobile phases were replaced as needed once consumed.

For each harvest day tested from each bioreactor, 0.75 mL of material was transferred to an autosampler vial and placed in the MIMICS-mPQA system. Each sample was injected for 1 cycle of analysis on the system to quantitate the 3 targeted attributes. The injection volume was kept consistent at 20 μL but the mass loads on each column were varied by applying varying online dilution factors ranging from 1:2 to 1:10 to target linear regions of each method based on prior development experience. In short, loads on the Pro A column were targeted at 10-25 μg, on the SEC column at 20-50 μg and on the RP column at 3-7 μg. For the Pro A titer method, a standard curve was run at the beginning of the total campaign and again at a second point upon Pro A buffer replacement for a total of 2 standard curves run for this entire campaign. The standard curve was constructed by various online dilutions of a stock anti-TGFβ DS at 2.5 mg/mL to create a curve from 2 to 50 μg on column.

The stock used for the standard curve was previously diluted for prior runs and kept in subaliquots at −80° C. for use on MIMICS-mPQA campaigns.

Results

Figure 10:
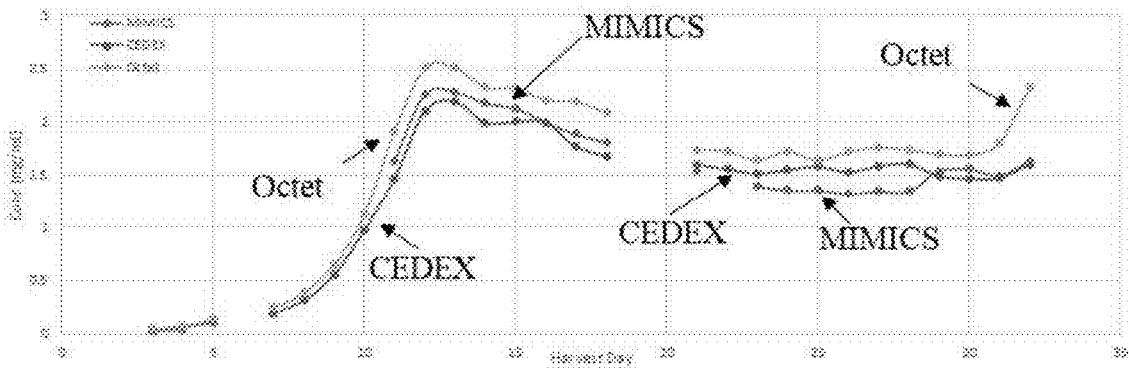
FIG. 10 is a graph comparing three titer methods (MIMICS-mPQA-blue; CEDEX™ Bioanalyzer-red; Octet-green) for a therapeutic monoclonal antibody 100 L bioreactor. All plotted data points on MIMICs-mPQA were frozen harvest. Data gaps represent samples that were not analyzed.
Figure 11:
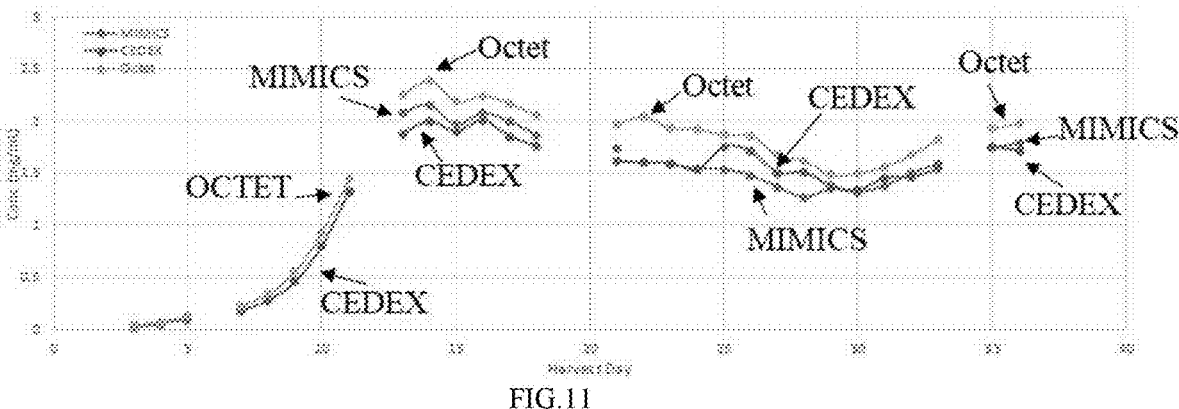
FIG. 11 is a graph comparing three titer methods (MIMICS-mPQA-blue; CEDEX™ Bioanalyzer-red; Octet-green) for a therapeutic monoclonal antibody 3 L bioreactor (V09). All plotted data points on MIMICs-mPQA were frozen harvest. Data gaps represent samples that were not analyzed.
Figure 12:
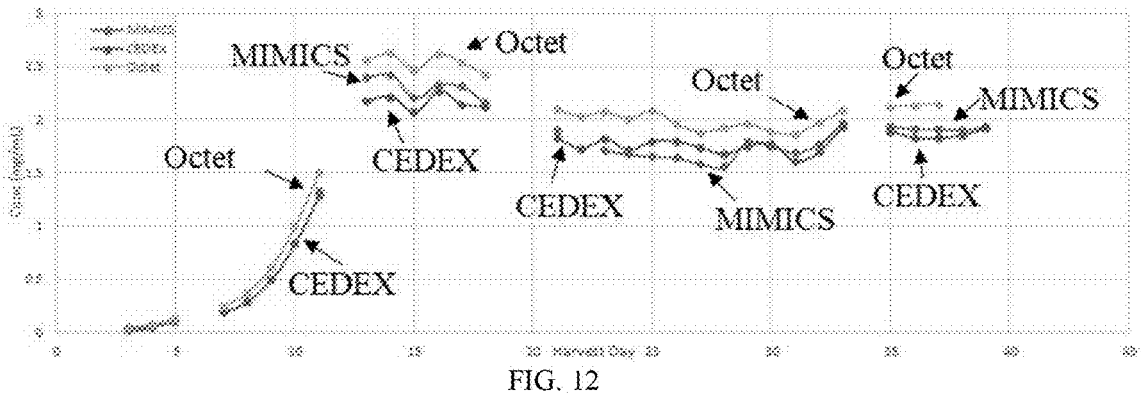
FIG. 12 is a graph comparing three titer methods (MIMICS-mPQA-blue; CEDEX™ Bioanalyzer-red; Octet-green) for a therapeutic monoclonal antibody 3 L bioreactor (V12). All plotted data points on MIMICS-mPQA were frozen harvest. Data gaps represent samples that were not analyzed.

The captured data from Pro A quantitation was also compared to two offline quantitative titer measurements: titer by measurement on Octet using Pro A biosensor tips and titer by CEDEX™ Bioanalyzer measurement. FIGS. 10-12 demonstrate the comparability of the MIMICS-mPQA titer as compared to the offline methods for the 100 L and 3 L bioreactors.

Overall, the trending was consistent between the 3 methods. When comparing the MIMICS-mPQA data to the CEDEX™ Bioanalyzer method, the % difference was less than 10% for all of the run which is an acceptable CV for an analytical method. The CEDEX™ Bioanalyzer is typically the method used for titer measurement for daily upstream process monitoring. The comparability of MIMICS-mPQA to this technique provided an orthogonal tool for titer determination for mammalian cultivation. The added advantage of MIMICS-mPQA was the decreased manual manipulation of the sample and potential bias of sample storage when testing is performed offline.

Figure 13:
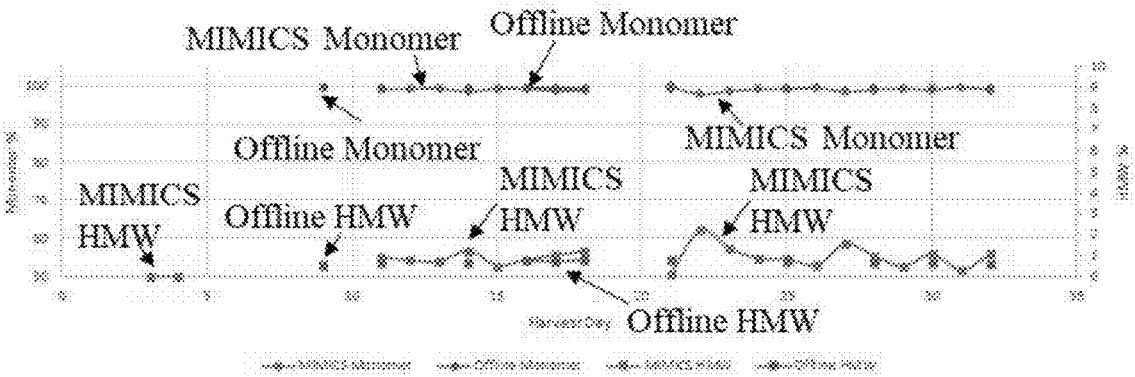
FIG. 13 is a graph comparing two aggregation methods (MIMICS-mPQA and offline method) for a therapeutic monoclonal antibody 100 L bioreactor. The graph compares two assay outputs: monomer percentage and high molecular weight (HMW) percentage. All plotted data points on MIMICS-mPQA were from frozen harvest. Data gaps represent samples that were not analyzed.
Figure 14:
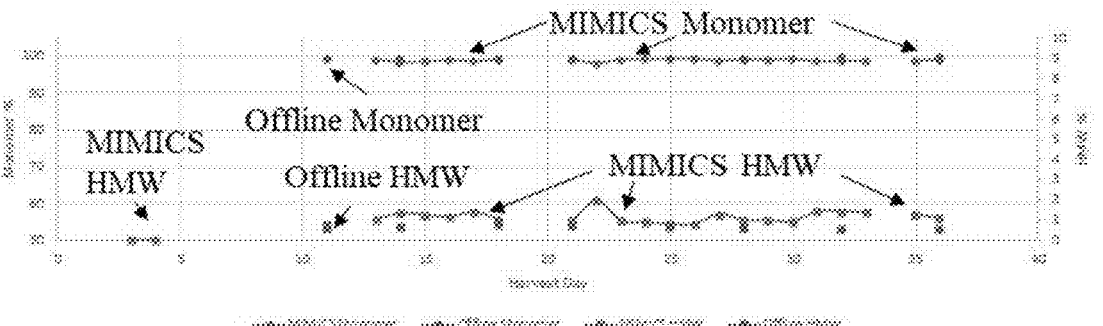
FIG. 14 is a graph comparing two aggregation methods (MIMICS-mPQA and offline method) for a therapeutic monoclonal antibody 3 L bioreactor (V09). The graph compares two assay outputs: monomer percentage and high molecular weight (HMW) percentage. All plotted data points on MIMICS-mPQA were from frozen harvest. Data gaps represent samples that were not analyzed.
Figure 15:
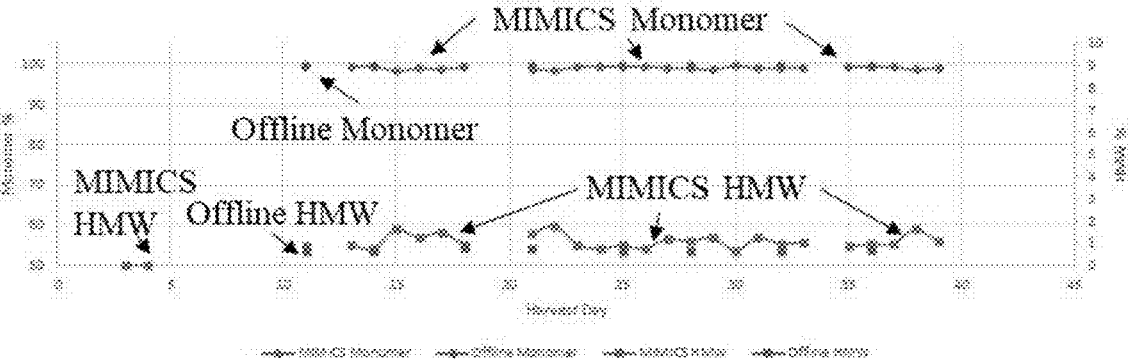
FIG. 15 is a graph comparing two aggregation methods (MIMICS-mPQA and offline method) for a therapeutic monoclonal antibody 3 L bioreactor (V12). The graph compares two assay outputs: monomer percentage and high molecular weight (HMW) percentage. All plotted data points on MIMICS-mPQA were from frozen harvest. Data gaps represent samples that were not analyzed.

The aggregation data captured in this experiment was compared to the offline SEC method run for normal process monitoring. The data for each bioreactor is presented in FIGS. 13-15.

Overall, the trending is comparable between the offline analytical method and MIMICS-mPQA. Both methods showed aggregation levels of less than 2.5% across the entire campaign. The MIMICS-mPQA system allowed for a greater number of data points to be acquired for this campaign than normally tested in offline analytics. This increased sampling allows for a deeper look at aggregation fluctuation over the course of the campaign.

Figure 16:
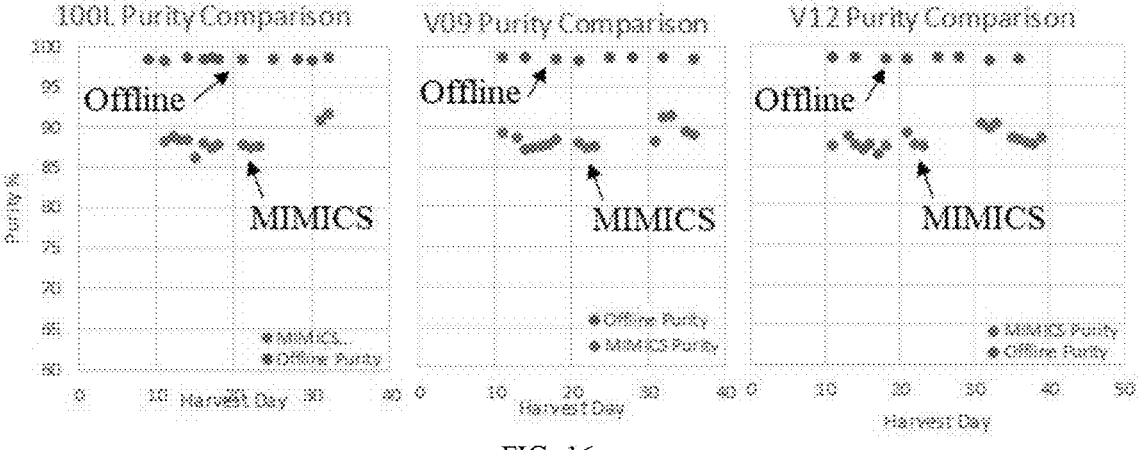
FIG. 16 is a graph comparing two purity methods (MIMICS-mPQA and offline method) for all bioreactors (100 L, 3 L V09, 3 L V12) from a therapeutic monoclonal antibody for overall % purity. All plotted data points on MIMICS-mPQA were from frozen harvest. Data gaps represent samples that were not analyzed.

The purity data captured from MIMICS-mPQA analysis was also compared to the offline purity method run for process monitoring as shown in FIG. 16. The offline method was based on CE-SDS methodology which is orthogonal to the purity measurement performed with MIMICS-mPQA.

As shown in FIG. 16, the MIMICS-mPQA system provides overall lower absolute percent purities compared to the offline method. Despite the absolute differences in percentage, the overall trending was consistent between both methods.

Overall, the MIMICS-mPQA system was successfully applied in an at-line monitoring mode to the 100 L pilot scale bioreactor campaign from anti-TGFβ. The system allowed for increased sampling compared to offline analyses which further allowed for greater process understanding over the course of the campaign. Additionally, the titer and aggregation methods were highly comparable to the offline analytics providing confidence in on the floor analyses compared to those obtained in an analytics laboratory. The MIMICS-mPQA system also allowed for decreased sample consumption and faster throughput as there was no need for a prior Protein A purification before analysis as this step is built into the overall MIMICS-mPQA workflow. Finally, the system was able to run over the course of 4 weeks with minimal incident further strengthening understanding of instrument robustness and column stability.

What is claimed is:

1. A method for measuring product quality attributes of an analyte of a biological sample, the method comprising:

obtaining a biological sample in a biological manufacturing system and delivering the biological sample to a first flow control device, wherein the first flow control device is configured to direct the biological sample either to a second flow control device or to a purification apparatus in fluid communication with the second flow control device;

delivering the biological sample to the second flow control device, wherein the second flow control device is configured to receive the biological sample either directly from the first flow control device or from the purification apparatus;

directing a first portion of the biological sample to a first sample analyzer via the second flow control device in fluid communication with the first flow control device, the purification apparatus, and the first sample analyzer, and obtaining information about a first product quality attribute of an analyte of the biological sample by analyzing the first portion of the biological sample in the first sample analyzer;

directing a second portion of the biological sample to a second sample analyzer in fluid communication with the second flow control device and obtaining information about a second product quality attribute of an analyte of the biological sample by analyzing the second portion of the biological sample in the second sample analyzer, wherein the first and second product quality attributes are different.

2. The method of claim 1, wherein the purification apparatus comprises an affinity chromatography column.

3. The method of claim 1, wherein the first sample analyzer comprises a first chromatography column.

4. The method of claim 3, wherein the first chromatography column comprises at least one member of the group consisting of a cation exchange chromatography column, a size exclusion chromatography column, and a reversed phase chromatograph column.

5. The method of claim 3, which comprises a quantification detector in fluid communication with the first chromatography column of the first sample analyzer, the method comprising generating, using the quantification detector, an electrical signal representative of an amount of an analyte in an eluate stream from the first chromatography column.

6. The method of claim 3, wherein the second sample analyzer comprises a second chromatography column that is different from the first chromatography column and comprises at least one member selected from the group consisting of a cation exchange chromatography column, a size exclusion chromatography column, a reversed phase chromatography column, and a hydrophilic interaction chromatography column.

7. The method of claim 1, wherein the first product quality attribute of the analyte is a concentration of the analyte in the biological sample, a measure of aggregation of the analyte in the biological sample, a measure of charge variants or heterogeneity of the analyte in the biological sample, or a measure of purity or integrity of the analyte in the biological sample.

8. The method of claim 2, wherein the affinity chromatography column comprises at least one member selected from the group consisting of a Protein A chromatography column, a Protein G chromatography column, and a receptor binding column.

9. The method of claim 1, comprising delivering a buffer solution to the first sample analyzer from a buffer reservoir when the first portion of the biological sample is directed into the first sample analyzer.

10. The method of claim 9, wherein the buffer solution has a pH of 4.0 or less.

11. The method of claim 1, wherein the analyte comprises a protein in the biological sample.

12. The method of claim 11, wherein the protein comprises an antibody in the biological sample.

13. The method of claim 1, wherein the biological sample is a harvest medium extracted from the bioreactor.

14. The method of claim 1, wherein the biological sample is a portion of a cell culture.

15. The method of claim 5, wherein generating an electrical signal representative of an amount of the analyte in the biological sample comprises measuring at least one of absorbance information and fluorescence information corresponding to the analyte.

16. The method of claim 5, wherein generating an electrical signal representative of an amount of the analyte in the biological sample comprises measuring ion abundance information corresponding to the analyte.

17. The method of claim 1, comprising directing additional portions of the biological sample into additional sample analyzers and obtaining information about at least one additional product quality attribute of the analyte of the biological sample.

18. The method of claim 17, wherein the at least one additional product quality attribute is different from the first and second product quality attributes and is selected from the group consisting of a concentration of the analyte in the biological sample, a measure of aggregation of the analyte in the biological sample, a measure of charge variants or heterogeneity of the analyte in the biological sample, or a measure of purity or integrity of the analyte in the biological sample.

19. The method of claim 1, which comprises obtaining the biological sample by extracting the biological sample from an operating bioreactor via the first flow control device, wherein the first flow control device is in fluid communication with the bioreactor.

20. The method of claim 1, wherein at least one of the first and second product quality attributes comprises a measure of charge variants or heterogeneity of the analyte in the biological sample, a measure of aggregation of the analyte in the biological sample, a measure of purity or integrity of the analyte in the biological sample, or a concentration of the analyte in the biological sample.

21. The method of claim 5, wherein the second sample analyzer comprises a second chromatography column that is different from the first chromatography column, wherein the second chromatography column is in fluid communication with a quantification detector, wherein the quantification detector is configured to generate an electrical signal representative of an amount of the analyte in the biological sample in an eluate stream from the second chromatography column.

22. The method of claim 21, wherein the first and second chromatography columns are in fluid communication with the same quantification detector.

\* \* \* \* \*